US011554055B2

(12) United States Patent
Bishop et al.

(10) Patent No.: US 11,554,055 B2
(45) Date of Patent: Jan. 17, 2023

(54) ABSORBENT ARTICLE WITH ABSORBENT BODY PROVIDING IMPROVED ACCESS TO CONTAINMENT POCKET OF WAIST CONTAINMENT MEMBER

(71) Applicant: Kimberly-Clark Worldwide, Inc., Neenah, WI (US)

(72) Inventors: David F. Bishop, Appleton, WI (US); Patsy A. Benedict, Waupun, WI (US); Joseph D. Coenen, Kaukauna, WI (US); Kaitlyn E. Mast, Neenah, WI (US); Michael J. Faulks, Neenah, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 493 days.

(21) Appl. No.: 16/702,927

(22) Filed: Dec. 4, 2019

(65) Prior Publication Data
US 2020/0107973 A1 Apr. 9, 2020

Related U.S. Application Data

(62) Division of application No. 15/511,720, filed as application No. PCT/US2016/047980 on Aug. 22, 2016, now abandoned.
(Continued)

(51) Int. Cl.
*A61F 13/494* (2006.01)
*A61F 13/511* (2006.01)
(Continued)

(52) U.S. Cl.
CPC ...... *A61F 13/51104* (2013.01); *A61F 13/494* (2013.01); *A61F 13/496* (2013.01);
(Continued)

(58) Field of Classification Search
CPC ............... A61F 13/494; A61F 13/4942; A61F 13/49466; A61F 13/496; A61F 13/533;
(Continued)

(56) References Cited

U.S. PATENT DOCUMENTS 3,395,708 A   8/1968   Laurence et al.
3,800,796 A   4/1974   Jacob
(Continued)

FOREIGN PATENT DOCUMENTS

CN   1200662 A   12/1998
CN   1853592 A   11/2006
(Continued)

OTHER PUBLICATIONS

Co-Pending U.S. Appl. No. 16/597,320, filed Oct. 9, 2019, by Jang et al. for "Absorbent Article with Selectively Positioned Waist Containment Member Having an Improved Waist Seal.".

*Primary Examiner* — Catharine L Anderson
(74) *Attorney, Agent, or Firm* — Kimberly-Clark Worldwide, Inc.

(57) ABSTRACT

An absorbent article (10, 110, 210, 310, 410) can include a waist containment member (54) and an absorbent body (34, 134, 234, 334, 434). The waist containment member (54) can include a proximal portion (76) and a distal portion (78) configured to freely move with respect to the chassis (11) when the absorbent article (10, 110, 210, 310, 410) is in a relaxed configuration to provide a containment pocket (82). The absorbent body (34, 134, 234, 334, 434) can be configured to provide improved access for exudates into the containment pocket (82) of the waist containment member (54).

13 Claims, 11 Drawing Sheets

Related U.S. Application Data

(60) Provisional application No. 62/212,051, filed on Aug. 31, 2015.

(51) Int. Cl.
  *A61F 13/53* (2006.01)
  *A61F 13/496* (2006.01)
  *A61F 13/534* (2006.01)
  *A61F 13/533* (2006.01)

(52) U.S. Cl.
  CPC .... *A61F 13/4942* (2013.01); *A61F 13/49466* (2013.01); *A61F 13/53* (2013.01); *A61F 13/534* (2013.01); *A61F 13/533* (2013.01); *A61F 2013/530481* (2013.01)

(58) Field of Classification Search
  CPC ............... A61F 13/534; A61F 13/536; A61F 2013/4948
  See application file for complete search history.

(56) References Cited

U.S. PATENT DOCUMENTS

| | | |
|---|---|---|
| 3,848,594 A | 11/1974 | Buell |
| 3,860,003 A | 1/1975 | Buell |
| 3,930,501 A | 1/1976 | Schaar |
| 3,978,861 A | 9/1976 | Schaar |
| 3,995,640 A | 12/1976 | Schaar |
| 4,074,716 A | 2/1978 | Schaar |
| 4,525,407 A | 6/1985 | Ness |
| 4,642,110 A | 2/1987 | Dudek |
| 4,643,729 A | 2/1987 | Laplanche |
| 4,657,539 A | 4/1987 | Hasse |
| 4,657,802 A | 4/1987 | Morman |
| 4,681,579 A | 7/1987 | Toussant et al. |
| 4,735,624 A | 4/1988 | Mazars |
| 4,738,677 A | 4/1988 | Foreman |
| 4,741,949 A | 5/1988 | Morman et al. |
| 4,753,646 A | 6/1988 | Enloe |
| 4,808,176 A | 2/1989 | Kielpikowski |
| 4,808,177 A | 2/1989 | DesMarais et al. |
| 4,822,435 A | 4/1989 | Igaue et al. |
| 4,850,990 A | 7/1989 | Huntoon et al. |
| 4,935,021 A | 6/1990 | Huffman et al. |
| 4,938,755 A | 7/1990 | Foreman |
| 4,977,011 A | 12/1990 | Smith |
| 5,026,364 A | 6/1991 | Robertson |
| 5,064,421 A | 11/1991 | Tracy |
| 5,069,672 A | 12/1991 | Wippler et al. |
| 5,106,385 A | 4/1992 | Allen et al. |
| 5,151,091 A | 9/1992 | Glaug et al. |
| 5,151,092 A | 9/1992 | Buell et al. |
| 5,187,817 A | 2/1993 | Zolner |
| 5,209,801 A | 5/1993 | Smith |
| 5,366,452 A | 11/1994 | Widlund et al. |
| 5,397,318 A | 3/1995 | Dreier |
| 5,413,570 A | 5/1995 | Enloe |
| 5,439,459 A | 8/1995 | Tanji et al. |
| 5,451,219 A | 9/1995 | Suzuki et al. |
| 5,514,104 A | 5/1996 | Cole et al. |
| 5,514,121 A | 5/1996 | Roe et al. |
| 5,531,730 A | 7/1996 | Dreier |
| 5,540,671 A | 7/1996 | Dreier |
| 5,558,660 A | 9/1996 | Dreier |
| 5,558,661 A | 9/1996 | Roe et al. |
| 5,569,227 A | 10/1996 | Vandemoortele et al. |
| 5,582,606 A | 12/1996 | Bruemmer et al. |
| 5,593,401 A | 1/1997 | Sosalla et al. |
| 5,624,422 A | 4/1997 | Allen |
| 5,643,242 A | 7/1997 | Lavon et al. |
| 5,649,918 A | 7/1997 | Schleinz |
| 5,667,503 A | 9/1997 | Roe et al. |
| 5,672,166 A | 9/1997 | Vandemoortele |
| 5,674,215 A | 10/1997 | Ronnberg |
| 5,685,873 A | 11/1997 | Bruemmer |
| 5,690,627 A | 11/1997 | Clear et al. |
| 5,695,488 A | 12/1997 | Sosalla |
| 5,776,121 A | 7/1998 | Roe et al. |
| 5,795,347 A | 8/1998 | Roe et al. |
| 5,817,086 A | 10/1998 | Kling |
| 5,827,259 A | 10/1998 | Laux et al. |
| 5,858,012 A | 1/1999 | Yamaki et al. |
| 5,895,382 A | 4/1999 | Popp et al. |
| 5,904,675 A | 5/1999 | Laux et al. |
| 5,931,826 A | 8/1999 | Faulks et al. |
| 5,938,652 A | 8/1999 | Sauer |
| 5,993,433 A | 11/1999 | St. Louis et al. |
| 6,103,952 A | 8/2000 | Coles et al. |
| 6,132,410 A | 10/2000 | Van Gompel et al. |
| 6,135,988 A | 10/2000 | Turner et al. |
| 6,142,985 A | 11/2000 | Feist |
| 6,149,638 A | 11/2000 | Vogt et al. |
| 6,174,303 B1 | 1/2001 | Suprise et al. |
| 6,217,563 B1 | 4/2001 | Van Gompel et al. |
| 6,258,076 B1 | 7/2001 | Glaug et al. |
| 6,264,639 B1 | 7/2001 | Sauer |
| 6,264,641 B1 * | 7/2001 | Van Gompel ..... A61F 13/53708 604/385.01 |
| 6,280,426 B1 | 8/2001 | Turner et al. |
| 6,293,937 B2 | 9/2001 | Matsushita et al. |
| 6,306,122 B1 | 10/2001 | Narawa et al. |
| 6,315,764 B1 | 11/2001 | Faulks et al. |
| 6,425,889 B1 | 7/2002 | Kitaoka et al. |
| 6,443,933 B1 | 9/2002 | Suzuki et al. |
| 6,455,753 B1 | 9/2002 | Glaug et al. |
| 6,458,114 B1 | 10/2002 | Mishima et al. |
| 6,482,194 B1 | 11/2002 | Putzer |
| 6,491,677 B1 | 12/2002 | Glaug et al. |
| 6,494,872 B1 | 12/2002 | Suzuki et al. |
| 6,506,185 B1 | 1/2003 | Sauer et al. |
| 6,527,756 B1 | 3/2003 | Mishima et al. |
| 6,638,262 B2 | 10/2003 | Suzuki et al. |
| 6,648,870 B2 | 11/2003 | Itoh et al. |
| 6,699,228 B1 | 3/2004 | Chmielewski et al. |
| 6,827,806 B2 | 12/2004 | Uitenbroek et al. |
| 6,838,591 B2 | 1/2005 | Waksmundzki et al. |
| 6,881,207 B1 | 4/2005 | Tracy |
| 6,890,327 B2 | 5/2005 | Suzuki et al. |
| 7,066,921 B2 | 6/2006 | Schmoker et al. |
| 7,166,093 B2 | 1/2007 | Drevik et al. |
| 7,166,095 B1 | 1/2007 | Coates |
| 7,247,152 B2 | 7/2007 | Klemp et al. |
| 7,604,625 B2 | 10/2009 | Turi et al. |
| 7,666,173 B2 | 2/2010 | Mishima et al. |
| 7,767,876 B2 | 8/2010 | Davis et al. |
| 7,842,021 B2 | 11/2010 | Wood et al. |
| 7,879,017 B1 | 2/2011 | Tabata et al. |
| 7,993,314 B2 | 8/2011 | Asp et al. |
| 8,075,543 B2 | 12/2011 | Okuda |
| 9,044,359 B2 * | 6/2015 | Wciorka ............... A61F 13/539 |
| 10,010,458 B2 | 7/2018 | Barnes |
| 10,159,610 B2 | 12/2018 | Barnes |
| 2001/0016720 A1 | 8/2001 | Otsubo |
| 2002/0045878 A1 | 4/2002 | Shimoe et al. |
| 2002/0082570 A1 | 6/2002 | Mishima et al. |
| 2002/0147438 A1 | 10/2002 | Tanaka et al. |
| 2003/0045853 A1 | 3/2003 | Sauer |
| 2003/0050616 A1 | 3/2003 | Reynolds et al. |
| 2003/0109844 A1 | 6/2003 | Gibbs |
| 2003/0119405 A1 | 6/2003 | Abuto et al. |
| 2004/0002690 A1 | 1/2004 | Miyamoto |
| 2004/0019343 A1 | 1/2004 | Olson et al. |
| 2004/0127882 A1 | 7/2004 | Weber |
| 2004/0243086 A1 | 12/2004 | VanGompel et al. |
| 2005/0027274 A1 | 2/2005 | Suzuki et al. |
| 2005/0148974 A1 | 7/2005 | Datta et al. |
| 2005/0215974 A1 | 9/2005 | O'Connell |
| 2005/0256488 A1 | 11/2005 | Sperl |
| 2006/0058738 A1 | 3/2006 | Ponzi et al. |
| 2006/0058767 A1 | 3/2006 | Zhang et al. |
| 2007/0093164 A1 | 4/2007 | Nakaoka |
| 2007/0112322 A1 | 5/2007 | Ashton et al. |
| 2007/0255245 A1 | 11/2007 | Asp et al. |

(56) References Cited

U.S. PATENT DOCUMENTS

| | | |
|---|---|---|
| 2007/0293832 A1 | 12/2007 | Wood et al. |
| 2008/0300560 A1 | 12/2008 | Magnusson et al. |
| 2010/0305533 A1 | 12/2010 | Ashton et al. |
| 2012/0277703 A1 | 11/2012 | Rhein et al. |
| 2012/0323207 A1 | 12/2012 | Takaishi |
| 2013/0012905 A1 | 1/2013 | Katsuragawa et al. |
| 2013/0012906 A1 | 1/2013 | Takino |
| 2013/0012907 A1 | 1/2013 | Sasayama et al. |
| 2013/0046266 A1 | 2/2013 | Kawakami |
| 2014/0018761 A1 | 1/2014 | Orchard, IV et al. |
| 2014/0121623 A1 | 5/2014 | Kirby et al. |
| 2014/0128829 A1 | 5/2014 | Miyake et al. |
| 2014/0257231 A1 | 9/2014 | Wang et al. |
| 2014/0350504 A1 | 11/2014 | Popp et al. |
| 2015/0051568 A1 | 2/2015 | Sakaguchi et al. |
| 2015/0182388 A1 | 7/2015 | Katsuragawa et al. |
| 2017/0000658 A1 | 1/2017 | Chatterjee et al. |
| 2017/0128281 A1 | 5/2017 | Takino et al. |
| 2017/0239104 A1 | 8/2017 | Jang et al. |
| 2017/0246054 A1 | 8/2017 | Bishop et al. |
| 2017/0296401 A1* | 10/2017 | Sugiyama ......... A61F 13/49012 |
| 2018/0055698 A1 | 3/2018 | Bishop et al. |
| 2018/0071155 A1 | 3/2018 | Bishop et al. |
| 2018/0104116 A1 | 4/2018 | Bishop et al. |
| 2019/0083331 A1 | 3/2019 | Barnes |

FOREIGN PATENT DOCUMENTS

| | | |
|---|---|---|
| CN | 102065811 A | 5/2011 |
| CN | 102065813 B | 11/2014 |
| CN | 204072501 U | 1/2015 |
| JP | 2001178772 A | 7/2001 |
| JP | 4754634 B2 | 8/2011 |
| KR | 100648562 B1 | 11/2006 |
| KR | 2020130001181 U | 2/2013 |
| WO | 9601607 A1 | 1/1996 |
| WO | 0037008 A1 | 6/2000 |
| WO | 2013021897 A1 | 2/2013 |
| WO | 2016159983 A1 | 10/2016 |

* cited by examiner

ABSORBENT ARTICLE WITH ABSORBENT BODY PROVIDING IMPROVED ACCESS TO CONTAINMENT POCKET OF WAIST CONTAINMENT MEMBER

RELATED APPLICATIONS

The present application is a divisional application and claims priority to U.S. patent application Ser. No. 15/511720, filed on Mar. 16, 2017, which is a national-phase entry, under 35 U.S.C. § 371, of PCT Patent Application No. PCT/US16/47980, filed on Aug. 22, 2016, which claims benefit of U.S. Provisional Application No. 62/212,051, filed Aug. 31, 2015, all of which are incorporated herein by reference.

TECHNICAL FIELD

The present disclosure relates to absorbent articles.

BACKGROUND OF THE DISCLOSURE

A primary function of personal care absorbent articles is to absorb and retain body exudates such as urine, fecal material, blood, and menses with additional desired attributes including low leakage of the exudates from the absorbent article and a dry feel to the wearer of the absorbent article. By preventing leakage of the exudates from the absorbent article, the absorbent article intends to prevent the body exudates from soiling or contaminating a wearer's or caregiver's clothing or other articles, such as bedding, that can come in contact with the wearer.

One common mode of failure is for exudates to leak out of the rear waist region or the front waist region of an absorbent article. As one example, fecal material that is not absorbed or contained by the absorbent article can move past the gaps between the absorbent article and the wearer's skin in the rear waist region and soil or contaminate the wearer's skin and clothing near their back. This may be more common of an occurrence for semi-solid fecal material, such as low viscosity fecal material, which can be prevalent with younger children. Such exudates can move around on the bodyside liner of an absorbent article under the influence of gravity, motion, force, and pressure by the wearer of the absorbent article. In such a circumstance, not only does the wearer's absorbent article need to be changed, but the wearer's clothing and/or bedding often also needs to be changed, resulting in additional work, expense, and stress for the caregiver.

Attempts have been made in the past to provide containment systems, especially on the bodyside liner or near the rear waist region to solve the problems described above. One example is by providing a waist elastic member and not adhering a portion of the waist containment member closest to the lateral axis of the absorbent article to the bodyside liner, such that the non-adhered portion of the waist elastic member can provide a containment pocket for exudates. One example of this configuration is a HUGGIES® Little Snugglers diaper. Although absorbent articles with such containment members intend to prevent leakage of exudates and have functioned adequately, failures can still occur.

Thus, there is a desire for improvements to containment systems and containment members of absorbent articles to prevent leakage of exudates, especially in the waist regions of the absorbent article. There is also a desire for improvements in containment systems to have increased void volumes to hold body exudates until the absorbent article can be changed.

SUMMARY OF THE DISCLOSURE

In one embodiment, an absorbent article can include a chassis including a body facing surface. The absorbent article can further include a waist containment member disposed on the body facing surface of the chassis. The waist containment member can include a first longitudinal side edge and a second longitudinal side edge. The second longitudinal side edge can be opposite from the first longitudinal side edge. The waist containment member can further include an upper lateral edge and a lower lateral edge. The upper lateral edge can be opposite from the lower lateral edge. The waist containment member can also include a proximal portion coupled to the body facing surface of the chassis and a distal portion being free to move with respect to the chassis when the absorbent article is in the relaxed configuration to provide a pocket for exudates. The absorbent article can include an absorbent body including a first end edge, a second end edge, and a pair of opposing longitudinal edges that extend between the first end edge and the second end edge. The first end edge of the absorbent body can include a first portion, a second portion, and an intermediate portion. The first portion and the second portion can each be disposed under waist containment member and the intermediate portion can be disposed to not be under the waist containment member.

In another embodiment, an absorbent article can include a chassis including a body facing surface. The absorbent article can further include a waist containment member disposed on the body facing surface of the chassis. The waist containment member can include a first longitudinal side edge and a second longitudinal side edge. The second longitudinal side edge can be opposite from the first longitudinal side edge. The waist containment member can further include an upper lateral edge and a lower lateral edge. The upper lateral edge can be opposite from the lower lateral edge. The waist containment member can also include a proximal portion coupled to the body facing surface of the chassis and a distal portion being free to move with respect to the chassis when the absorbent article is in the relaxed configuration to provide a pocket for exudates. The absorbent article can include an absorbent body including a first end edge and a second end edge. The absorbent body can also include a pair of opposing longitudinal edges that extend between the first end edge and the second end edge. The absorbent body can further include a first section having a first thickness and a second section having a second thickness. The first section and the second section can each at least partially be disposed under the waist containment member. The absorbent body can also include an intermediate section between the first section and the second section. A thickness of the intermediate section can be less than the first thickness and less than the second thickness. At least a portion of the intermediate section can be disposed under the waist containment member.

BRIEF DESCRIPTION OF DRAWINGS

A full and enabling disclosure thereof, directed to one of ordinary skill in the art, is set forth more particularly in the remainder of the specification, which makes reference to the appended figures in which.

Figure 1:
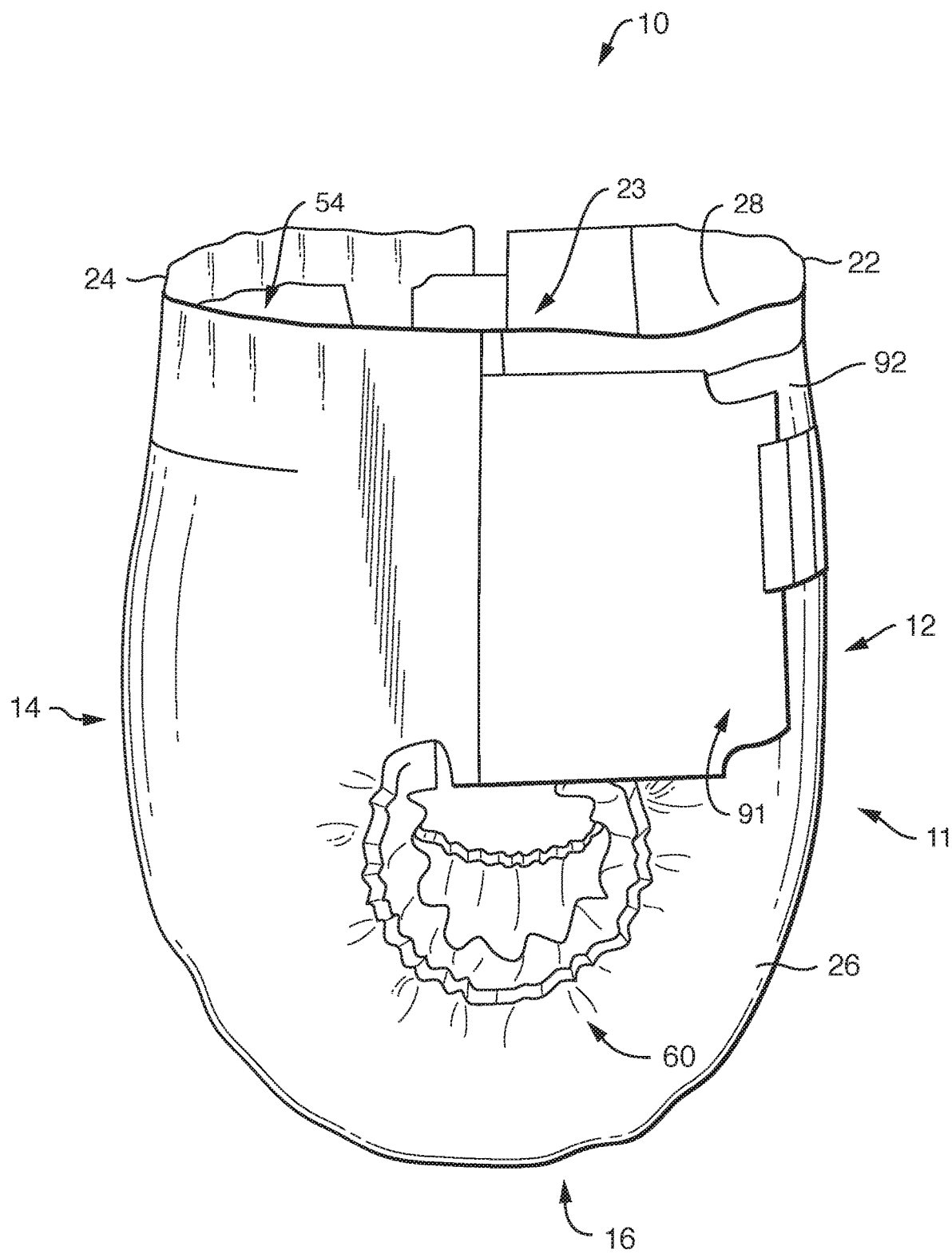
FIG. 1 is side perspective view of an exemplary embodiment of an absorbent article, such as a diaper, in a fastened condition.

Repeat use of reference characters in the present specification and drawings is intended to represent the same or analogous features or elements of the disclosure.

DETAILED DESCRIPTION OF THE DISCLOSURE

In an embodiment, the present disclosure is generally directed towards an absorbent article having an absorbent body and a waist containment member that can provide a containment pocket. In conjunction with the absorbent body, the waist containment member can provide a low compression resistance zone that can provide easier access for body exudates to enter the containment pocket. The absorbent body and the waist containment member can also provide increased void volume for body exudates. Each example is provided by way of explanation and is not meant as a limitation. For example, features illustrated or described as part of one embodiment or figure can be used on another embodiment or figure to yield yet another embodiment. It is intended that the present disclosure include such modifications and variations.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

Definitions:

The term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, diaper pants, training pants, youth pants, swim pants, feminine hygiene products, including, but not limited to, menstrual pads or pants, incontinence products, medical garments, surgical pads and bandages, other personal care or health care garments, and the like without departing from the scope of the present disclosure.

The term "acquisition layer" refers herein to a layer capable of accepting and temporarily holding liquid body exudates to decelerate and diffuse a surge or gush of the liquid body exudates and to subsequently release the liquid body exudates therefrom into another layer or layers of the absorbent article.

The term "bonded" or "coupled" refers herein to the joining, adhering, connecting, attaching, or the like, of two elements. Two elements will be considered bonded or coupled together when they are joined, adhered, connected, attached, or the like, directly to one another or indirectly to one another, such as when each is directly bonded to intermediate elements. The bonding or coupling of one element to another can occur via continuous or intermittent bonds.

The term "carded web" refers herein to a web containing natural or synthetic staple length fibers typically having fiber lengths less than about 100 mm. Bales of staple fibers can undergo an opening process to separate the fibers which are then sent to a carding process which separates and combs the fibers to align them in the machine direction after which the fibers are deposited onto a moving wire for further processing. Such webs are usually subjected to some type of bonding process such as thermal bonding using heat and/or pressure. In addition to or in lieu thereof, the fibers may be subject to adhesive processes to bind the fibers together such as by the use of powder adhesives. The carded web may be subjected to fluid entangling, such as hydroentangling, to further intertwine the fibers and thereby improve the integrity of the carded web. Carded webs, due to the fiber alignment in the machine direction, once bonded, will typically have more machine direction strength than cross machine direction strength.

The term "film" refers herein to a thermoplastic film made using an extrusion and/or forming process, such as a cast film or blown film extrusion process. The term includes apertured films, slit films, and other porous films which constitute liquid transfer films, as well as films which do not transfer fluids, such as, but not limited to, barrier films, filled films, breathable films, and oriented films.

The term "gsm" refers herein to grams per square meter.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "liquid impermeable" refers herein to a layer or multi-layer laminate in which liquid body exudates, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable.

The term "meltblown" refers herein to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers which may be continuous or discontinuous, are generally smaller than about 0.6 denier, and may be tacky and self-bonding when deposited onto a collecting surface.

The term "nonwoven" refers herein to materials and webs of material which are formed without the aid of a textile weaving or knitting process. The materials and webs of materials can have a structure of individual fibers, filaments, or threads (collectively referred to as "fibers") which can be interlaid, but not in an identifiable manner as in a knitted fabric. Nonwoven materials or webs can be formed from many processes such as, but not limited to, meltblowing processes, spunbonding processes, carded web processes, etc.

The term "pliable" refers herein to materials which are compliant and which will readily conform to the general shape and contours of the wearer's body.

The term "spunbond" refers herein to small diameter fibers which are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that are described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an embodiment, between about 0.6, 5 and 10 and about 15, 20 and 40. Spunbond fibers are generally not tacky when they are deposited on a collecting surface.

The term "superabsorbent" refers herein to a water-swellable, water-insoluble organic or inorganic material capable, under the most favorable conditions, of absorbing at least about 15 times its weight and, in an embodiment, at least about 30 times its weight, in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds, such as cross-linked polymers.

The term "thermoplastic" refers herein to a material which softens and which can be shaped when exposed to heat and which substantially returns to a non-softened condition when cooled.

The term "user" or "caregiver" refers herein to one who fits an absorbent article, such as, but not limited to, a diaper, diaper pant, training pant, youth pant, incontinent product, or other absorbent article about the wearer of one of these absorbent articles. A user and a wearer can be one and the same person.

Absorbent Article:

Referring to FIGS. 1-10, a non-limiting illustration of an absorbent article 10, 110, 210, 310 for example, a diaper, is illustrated. Other embodiments of the absorbent article could include training pants, diaper pants, youth pants, adult incontinence garments, and feminine hygiene articles. While the embodiments and illustrations described herein may generally apply to absorbent articles manufactured in the product longitudinal direction, which is hereinafter called the machine direction manufacturing of a product, it should be noted that one of ordinary skill in the art could apply the information herein to absorbent articles manufactured in the latitudinal direction of the product, which hereinafter is called the cross direction manufacturing of a product, without departing from the spirit and scope of the disclosure. For example, the absorbent article 410 in FIGS. 11 and 12 provides an exemplary embodiment of an absorbent article 410 that can be manufactured in cross-direction manufacturing process.

Figure 5:
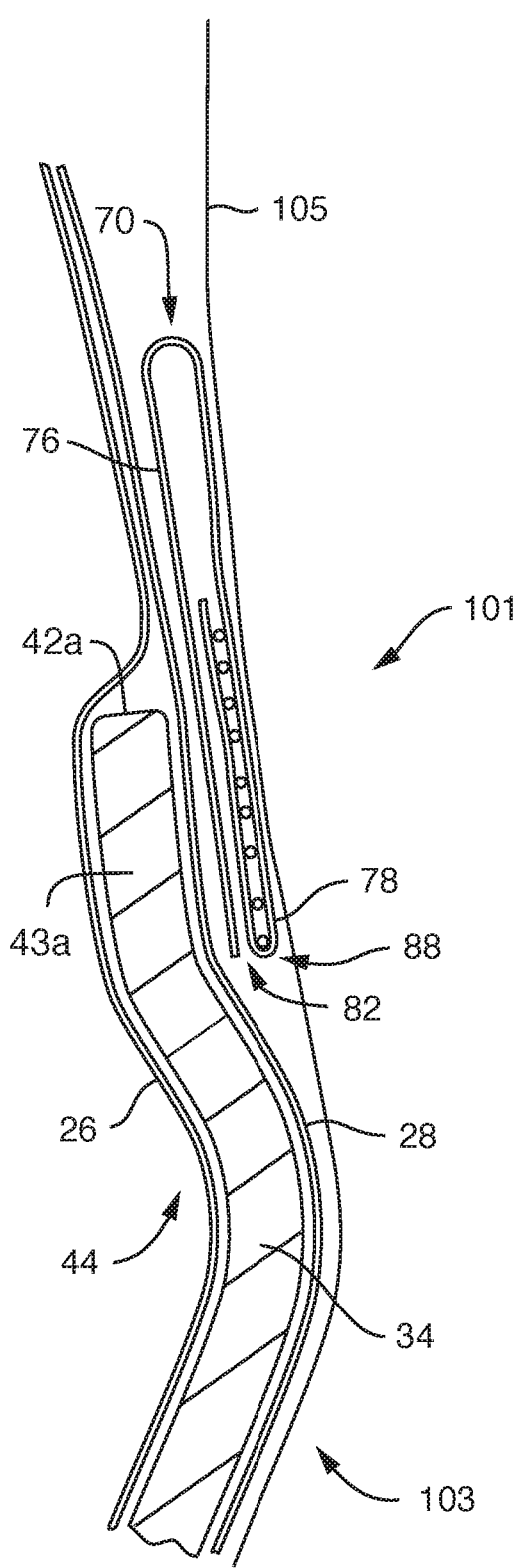
FIG. 5 is a cross-sectional view showing the back waist region of the absorbent article of FIG. 1 in a fastened condition against a wearer's buttocks and back, where the cross-section is taken in a high compression resistance zone similar to FIG. 3.
Figure 6:
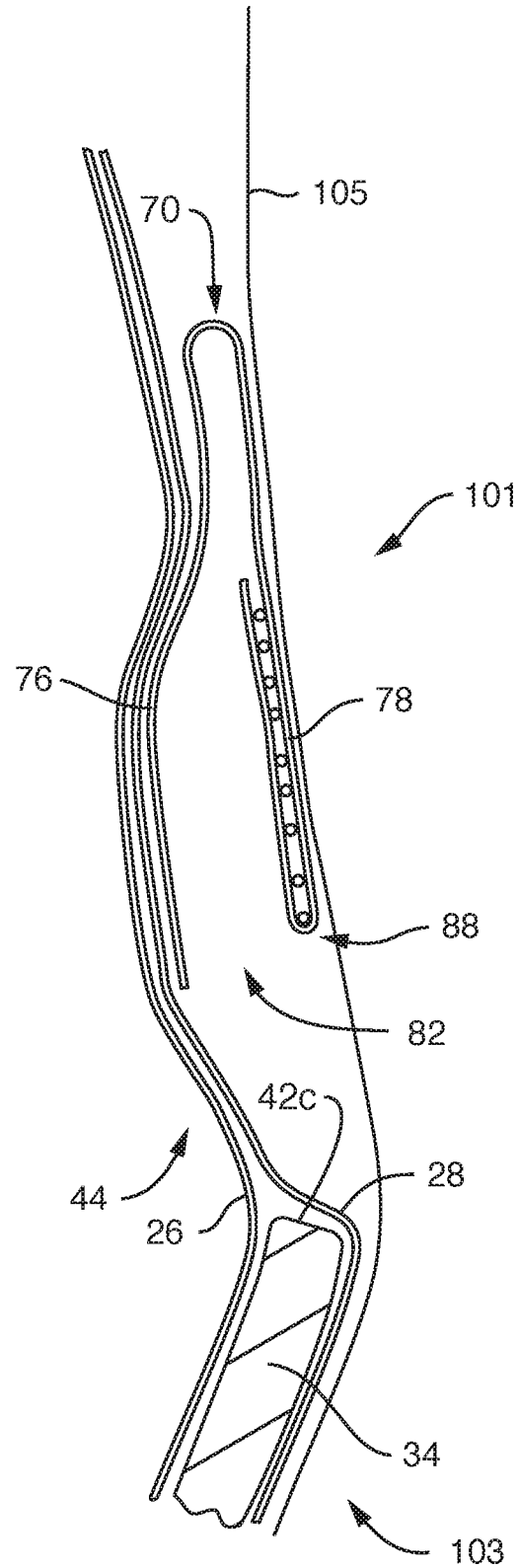
FIG. 6 is a cross-sectional view showing the back waist region of the absorbent article of FIG. 1 in a fastened condition against a wearer's buttocks and back, where the cross-section is taken in a low compression resistance zone similar to FIG. 4.
Figure 7:
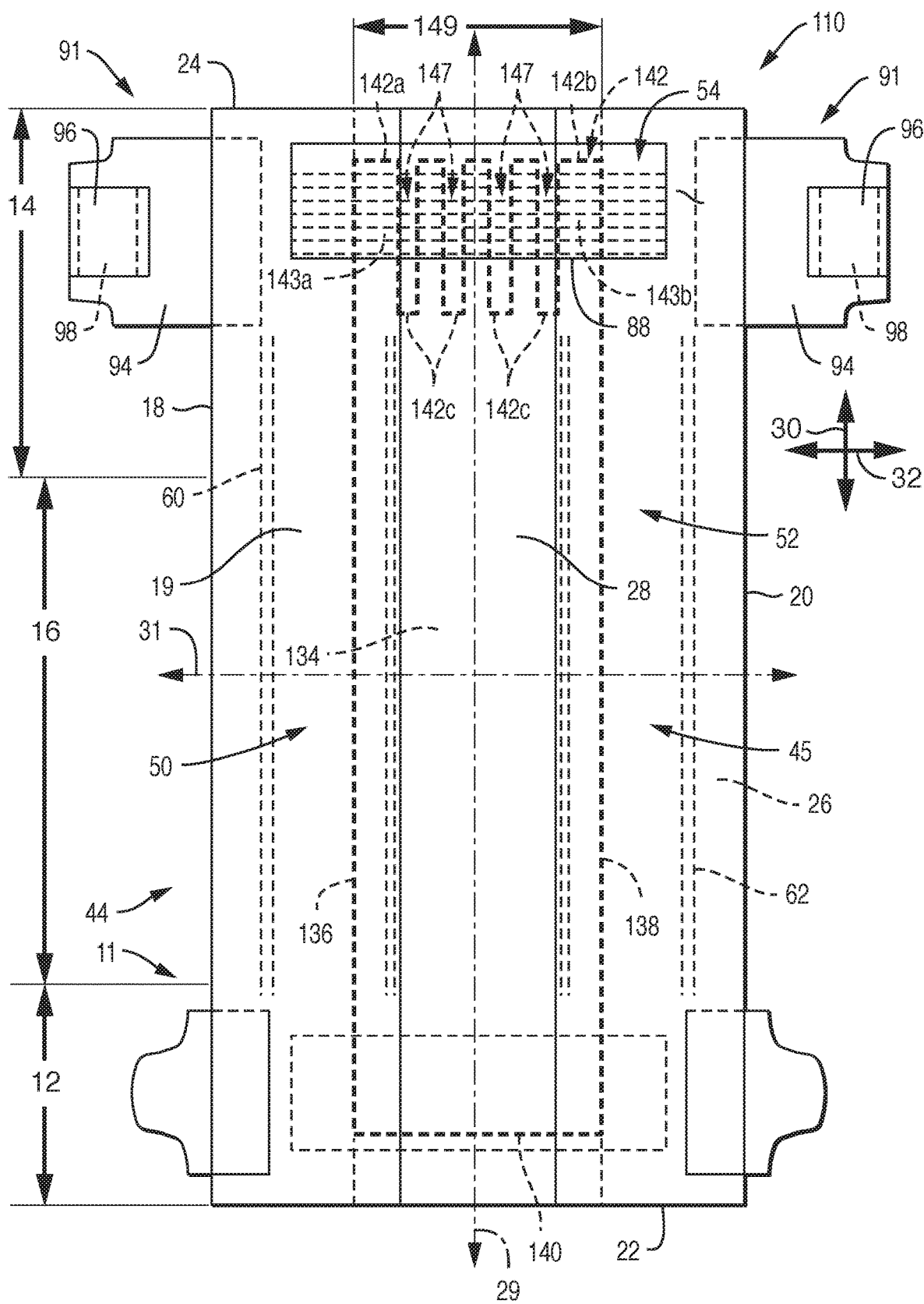
FIG. 7 is a top plan view of an alternative embodiment of an absorbent article in a stretched, laid flat, unfastened condition.
Figure 8:
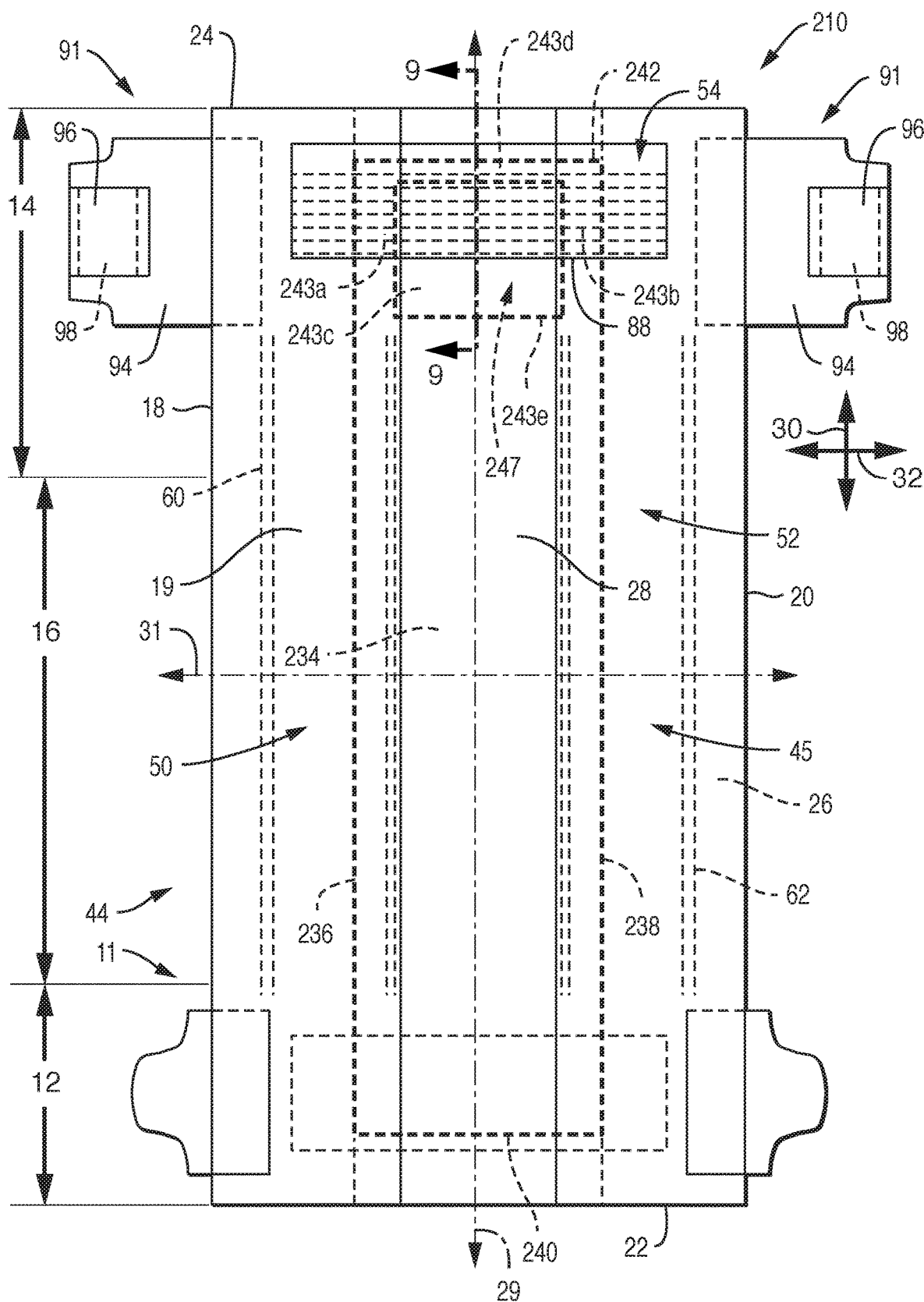
FIG. 8 is a top plan view of another alternative embodiment of an absorbent article in a stretched, laid flat, unfastened condition.
Figure 9:
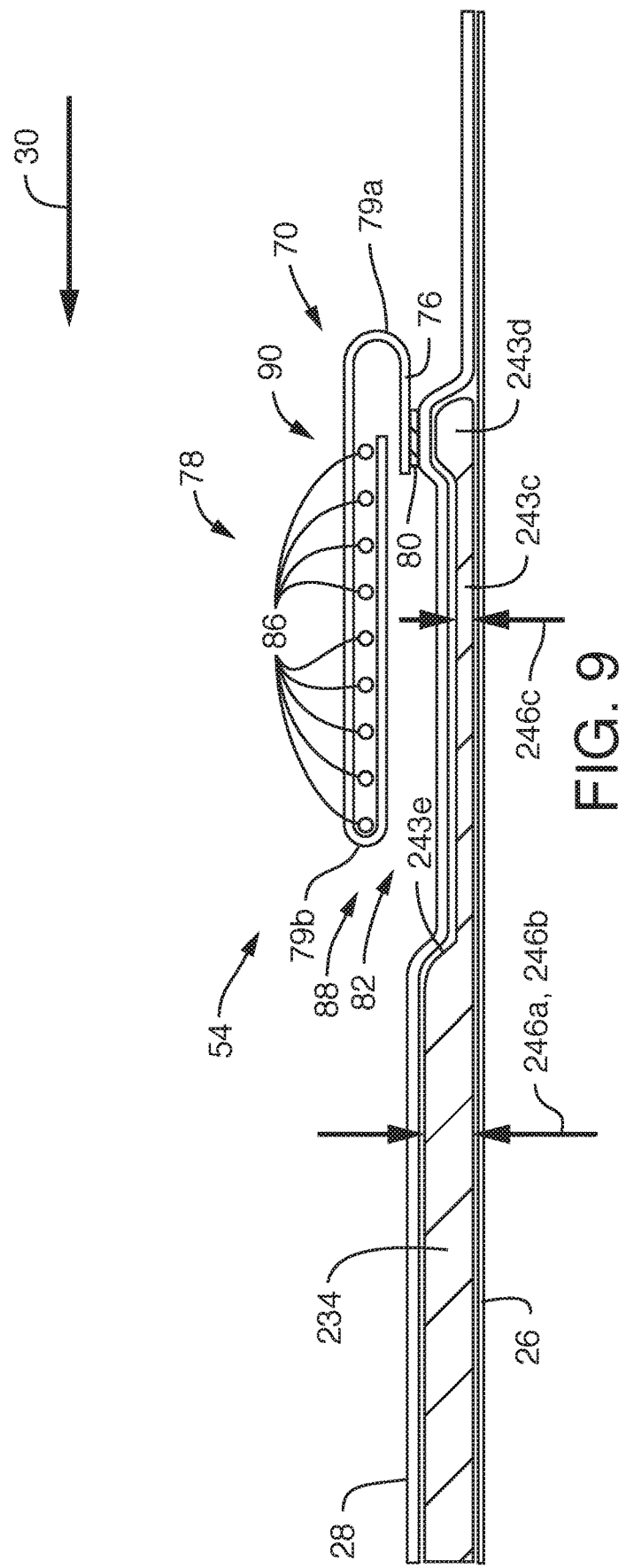
FIG. 9 is a cross-sectional view taken along line 9-9 from FIG. 8.
Figure 10:
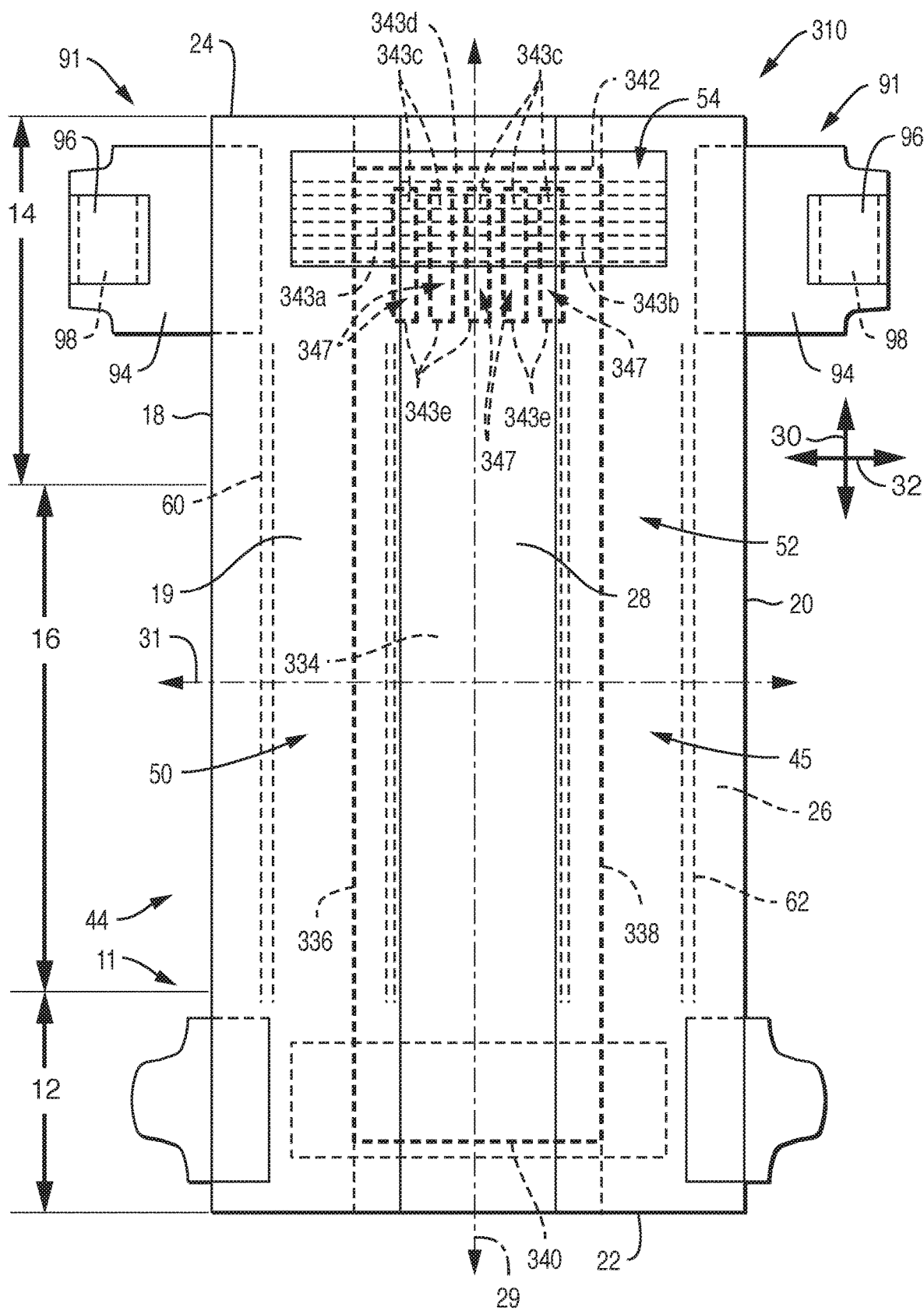
FIG. 10 is a top plan view of yet another alternative embodiment of an absorbent article in a stretched, laid flat, unfastened condition.
Figure 11:
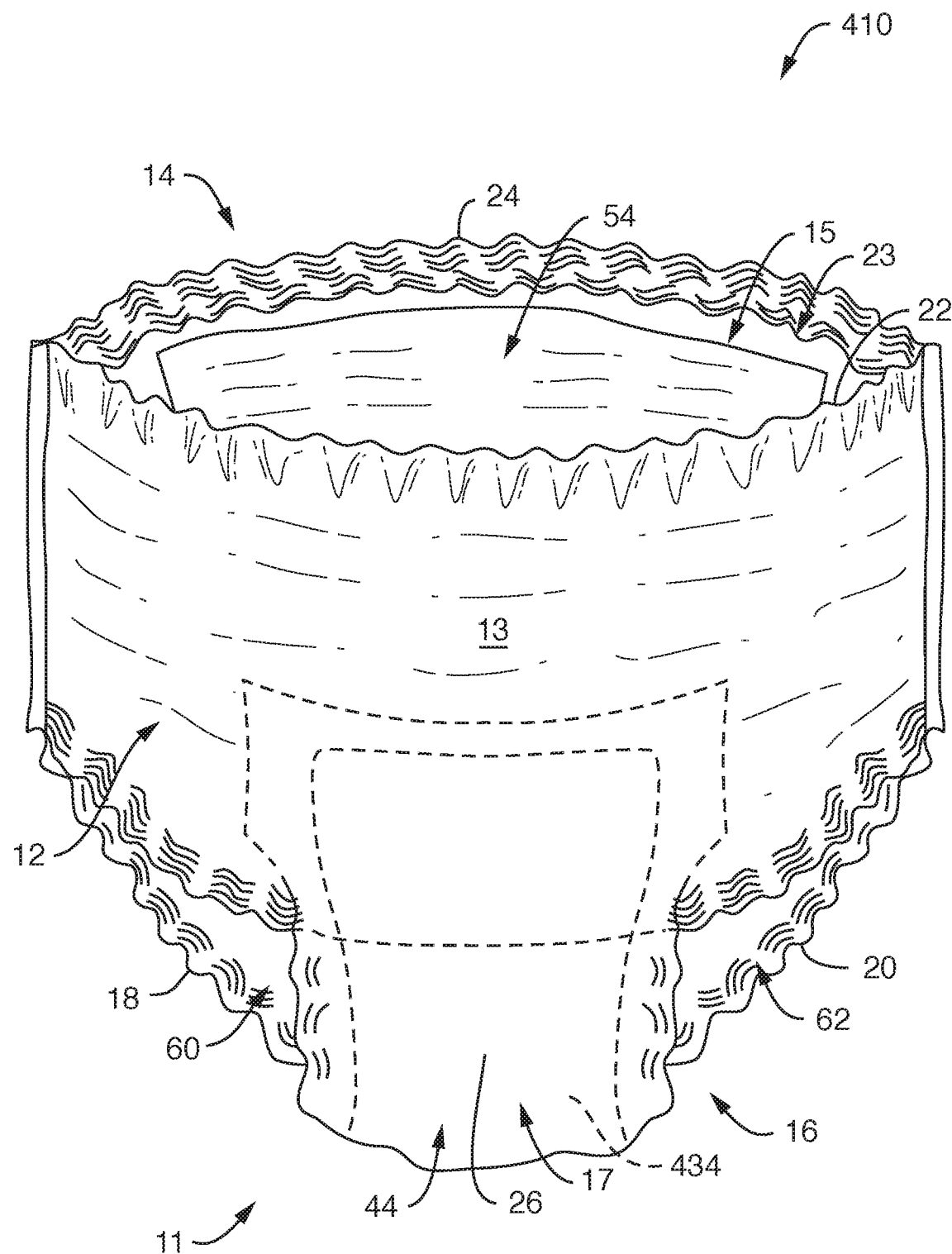
FIG. 11 is a front perspective view of an alternative embodiment of an absorbent article, such as a pant.
Figure 12:
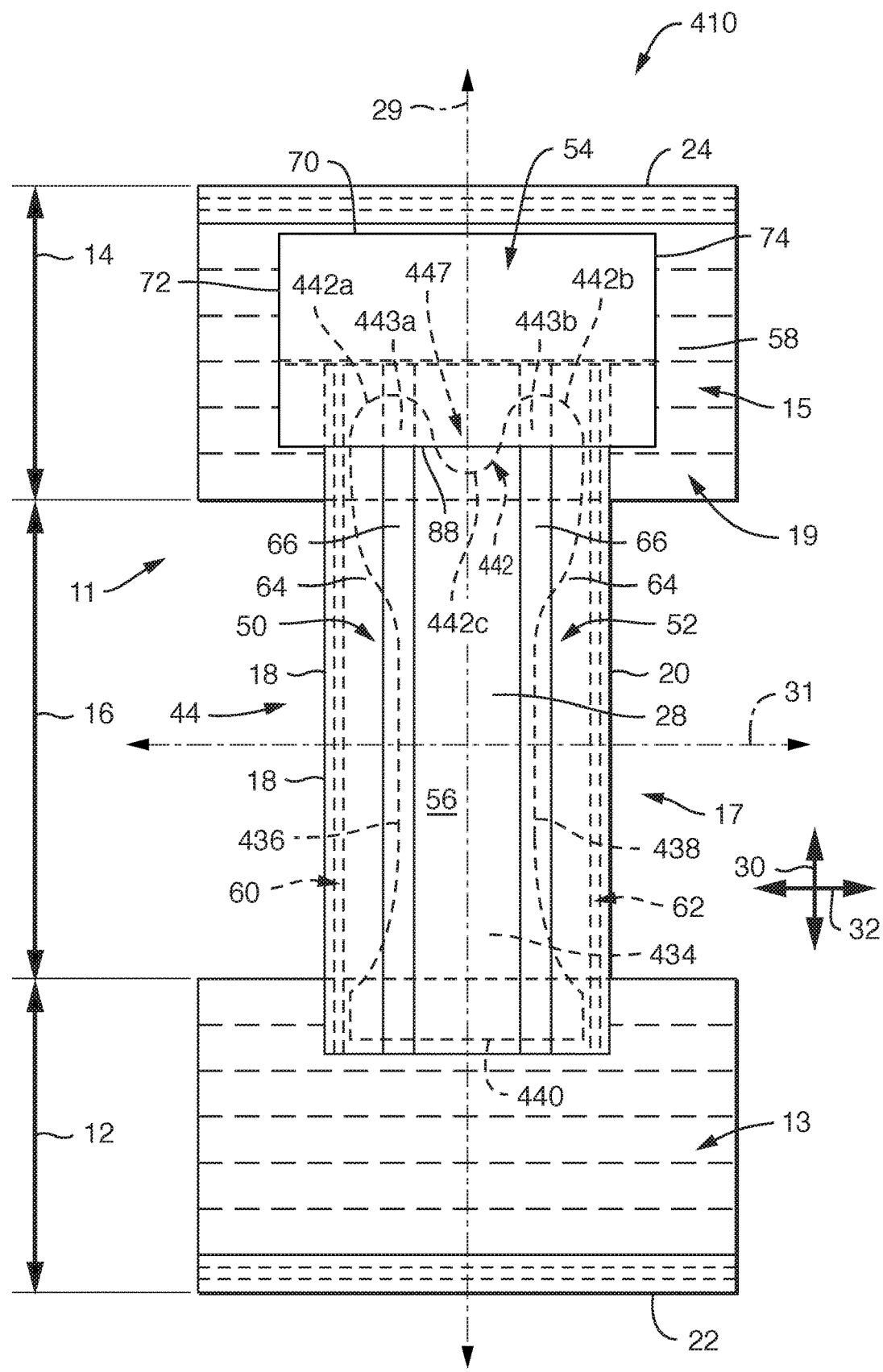
FIG. 12 is a top plan view of the absorbent article of FIG. 11 in a stretched, laid flat condition.

The absorbent article 10 illustrated in FIGS. 1-6, the absorbent article 110 in FIG. 7, the absorbent article 210 of FIGS. 8 and 9, the absorbent article 310 of FIG. 10, and the absorbent article 410 of FIGS. 11 and 12 can each include a chassis 11. The absorbent article 10, 110, 210, 310, 410 can include a front waist region 12, a rear waist region 14, and a crotch region 16 disposed between the front waist region 12 and the rear waist region 14 and interconnecting the front and rear waist regions, 12, 14, respectively. The front waist region 12 can be referred to as the front end region, the rear waist region 14 can be referred to as the rear end region, and the crotch region 16 can be referred to as the intermediate region. In the embodiment depicted in FIGS. 11 and 12, a three-piece construction of an absorbent article 410 is depicted where the absorbent article 410 can have a chassis 11 including a front waist panel 13 defining the front waist region 12, a rear waist panel 15 defining the rear waist region 14, and an absorbent panel 17 defining the crotch region 16 of the absorbent article 410. The absorbent panel 17 can extend between the front waist panel 13 and the rear waist panel 15. In some embodiments, the absorbent panel 17 can overlap the front waist panel 13 and the rear waist panel 15. The absorbent panel 17 can be bonded to the front waist panel 13 and the rear waist panel 15 to define a three-piece construction. However, it is contemplated that an absorbent article can be manufactured in a cross-direction without being a three-piece construction garment.

The absorbent article 10, 110, 210, 310, 410 can have a pair of longitudinal side edges 18, 20, and a pair of opposite waist edges, respectively designated front waist edge 22 and rear waist edge 24. The front waist region 12 can be contiguous with the front waist edge 22 and the rear waist region 14 can be contiguous with the rear waist edge 24. The longitudinal side edges 18, 20 can extend from the front waist edge 22 to the rear waist edge 24. The longitudinal side edges 18, 20 can extend in a direction parallel to the longitudinal direction 30 for their entire length, such as for the absorbent articles 10, 110, 310 illustrated in FIGS. 2, 7, 8, and 10. In other embodiments, the longitudinal side edges 18, 20 can be curved between the front waist edge 22 and the rear waist edge 24. In the absorbent article 410 of FIGS. 11 and 12, the longitudinal side edges 18, 20 can include portions of the front waist panel 13, the absorbent panel 17, and the rear waist panel 15.

The front waist region 12 can include the portion of the absorbent article 10, 110, 210, 310, 410 that, when worn, is positioned at least in part on the front of the wearer while the rear waist region 14 can include the portion of the absorbent article 10, 110, 210, 310, 410 that, when worn, is positioned at least in part on the back of the wearer. The crotch region 16 of the absorbent article 10, 110, 210, 310, 410 can include the portion of the absorbent article 10, 110, 210, 310, 410 that, when worn, is positioned between the legs of the wearer and can partially cover the lower torso of the wearer. The waist edges, 22 and 24, of the absorbent article 10, 110, 210, 310, 410 are configured to encircle the waist of the wearer and together define a central waist opening 23 (as labeled in FIG. 1 and FIG. 11) for the waist of the wearer. Portions of the longitudinal side edges 18, 20 in the crotch region 16 can generally define leg openings for the legs of the wearer when the absorbent article 10, 110, 210, 310, 410 is worn.

The absorbent article 10, 110, 210, 310, 410 can include an outer cover 26 and a bodyside liner 28. The outer cover 26 and the bodyside liner 28 can form a portion of the chassis 11. In an embodiment, the bodyside liner 28 can be bonded to the outer cover 26 in a superposed relation by any suitable means such as, but not limited to, adhesives, ultrasonic bonds, thermal bonds, pressure bonds, or other conventional techniques. The outer cover 26 can define a length in a longitudinal direction 30, and a width in the lateral direction 32, which, in the illustrated embodiment, can coincide with the length and width of the absorbent article 10, 110, 310, 410. As illustrated in FIGS. 2, 7, 8, 9, and 12, the absorbent article 10, 110, 210, 310, 410 can have a longitudinal axis 29 extending in the longitudinal direction 30 and a lateral axis 31 extending in the lateral direction 32.

The chassis 11 can include an absorbent body 34, 134, 234, 334, 434. Much of the description herein for absorbent bodies will be applicable to several embodiments of an absorbent body 34, 134, 234, 334, 434, however, the discussion will focus on absorbent body 34 illustrated in FIGS. 2-6. That same discussion of the absorbent body 34 can apply to other embodiments of absorbent bodies 134, 234, 334, 434 unless otherwise noted.

The absorbent body 34 can be disposed between the outer cover 26 and the bodyside liner 28. The absorbent body 34 can have longitudinal edges, 36 and 38, which, in an embodiment, can form portions of the longitudinal side edges, 18 and 20, respectively, of the absorbent article 10. The absorbent body 34 can have a first end edge 40 that is opposite a second end edge 42, respectively, which, in an embodiment, can form portions of the waist edges, 22 and 24, respectively, of the absorbent article 10. In some embodiments, the first end edge 40 can be in the front waist region 12. In some embodiments, the second end edge 42 can be in the rear waist region 14. In an embodiment, the absorbent body 34 can have a length and width that are the same as or less than the length and width of the absorbent article 10. The bodyside liner 28, the outer cover 26, and the absorbent body 34 can form part of an absorbent assembly 44. In the absorbent article 410 of FIGS. 11 and 12, the absorbent panel 17 can form the absorbent assembly 44. The absorbent assembly 44 can also include a fluid transfer layer (not shown) and a fluid acquisition layer (not shown) between the bodyside liner 28 and the fluid transfer layer (if present) as is known by one of ordinary skill in the art. The absorbent assembly 44 can also include a spacer layer (not shown) disposed between the absorbent body 34 and the outer cover 26 as is known by one of ordinary skill in the art.

The absorbent article 10, 110, 210, 310, 410 can be configured to contain and/or absorb liquid, solid, and semi-solid body exudates discharged from the wearer. In some embodiments, containment flaps 50, 52 can be configured to provide a barrier to the lateral flow of body exudates. To further enhance containment and/or absorption of body exudates, the absorbent article 10, 110, 210, 310, 410 can suitably include a waist containment member 54. In some embodiments, the waist containment member 54 can be disposed in the rear waist region 14 of the absorbent article 10, 110, 210, 310, 410. In some embodiments, a waist containment member 54 can be disposed in the front waist region 12. In some embodiments, such as the absorbent article 10 illustrated in FIG. 2, a waist containment member 54 can be disposed in the front waist region 12 and a waist containment member 54 can be disposed in the rear waist region 14.

The waist containment member 54 can be disposed on the body facing surface 19 of the chassis 11 to help contain and/or absorb body exudates. In some embodiments, such as in the absorbent articles 10, 110, 210, 310 depicted in FIGS. 1-10, the waist containment member 54 can be disposed on the body facing surface 45 of the absorbent assembly 44. In some embodiments, the waist containment member 54 can be disposed on the body facing surface 56 of the bodyside liner 28. In some embodiments, such as in the absorbent article 410 depicted in FIGS. 11 and 12, the waist containment member 54 can be disposed on the body facing surface 58 of the rear waist panel 15.

As will be discussed in greater detail below, the waist containment member 54 can include a proximal portion 76 and distal portion 78. The proximal portion 76 can be coupled to the body facing surface 19 of the chassis 11 and the distal portion 78 can be free to move with respect to the chassis 11 when the absorbent article 10, 110, 210, 310, 410 is in a relaxed configuration to provide a containment pocket 82 for exudates.

The absorbent article 10, 110, 210, 310, 410 can further include leg elastic members 60, 62 as are known to those of ordinary skill in the art. The leg elastic members 60, 62 can be attached to the outer cover 26 and/or the bodyside liner 28 along the opposite longitudinal side edges, 18 and 20, and positioned in the crotch region 16 of the absorbent article 10, 110, 210, 310, 410. The leg elastic members 60, 62 can be parallel to the longitudinal axis 29 as shown in FIGS. 2, 7, 8, 10, and 12 or can be curved as is known by one of ordinary skill in the art. The leg elastic members 60, 62 can provide elasticized leg cuffs.

Additional details regarding each of these elements of the absorbent article 10, 110, 210, 310, 410 described herein can be found below and with reference to the FIGS. 1 through 12.

Outer Cover:

The outer cover 26 and/or portions thereof can be breathable and/or liquid impermeable. The outer cover 26 and/or portions thereof can be elastic, stretchable, or non-stretchable. The outer cover 26 may be constructed of a single layer, multiple layers, laminates, spunbond fabrics, films, meltblown fabrics, elastic netting, microporous webs, bonded-carded webs or foams provided by elastomeric or polymeric materials. In an embodiment, for example, the outer cover 26 can be constructed of a microporous polymeric film, such as polyethylene or polypropylene.

In an embodiment, the outer cover 26 can be a single layer of a liquid impermeable material, such as a polymeric film. In an embodiment, the outer cover 26 can be suitably stretchable, and more suitably elastic, in at least the lateral direction 32. In an embodiment, the outer cover 26 can be stretchable, and more suitably elastic, in both the lateral 32 and the longitudinal 30 directions. In an embodiment, the outer cover 26 can be a multi-layered laminate in which at least one of the layers is liquid impermeable. In some embodiments, the outer cover 26 can be a two layer construction, including an outer layer (not shown) and an inner layer (not shown) which can be bonded together such as by a laminate adhesive. Suitable laminate adhesives can be applied continuously or intermittently as beads, a spray, parallel swirls, or the like, but it is to be understood that the inner layer can be bonded to the outer layer by other bonding methods, including, but not limited to, ultrasonic bonds, thermal bonds, pressure bonds, or the like.

The outer layer of the outer cover 26 can be any suitable material and may be one that provides a generally cloth-like texture or appearance to the wearer. An example of such material can be a 100% polypropylene bonded-carded web with a diamond bond pattern available from Sandler A. G., Germany, such as 30 gsm Sawabond 4185® or equivalent. Another example of material suitable for use as an outer layer of an outer cover 26 can be a 20 gsm spunbond polypropylene non-woven web. The outer layer may also be constructed of the same materials from which the bodyside liner 28 can be constructed as described herein.

The liquid impermeable inner layer of the outer cover 26 (or the liquid impermeable outer cover 26 where the outer cover 26 is of a single-layer construction) can be either vapor permeable (i.e., "breathable") or vapor impermeable. The liquid impermeable inner layer (or the liquid impermeable outer cover 26 where the outer cover 26 is of a single-layer construction) can be manufactured from a thin plastic film. The liquid impermeable inner layer (or the liquid impermeable outer cover 26 where the outer cover 26 is of a single-layer construction) can inhibit liquid body exudates from leaking out of the absorbent article 10, 110, 210, 310, 410 and wetting articles, such as bed sheets and clothing, as well as the wearer and caregiver.

In some embodiments, where the outer cover 26 is of a single layer construction, it can be embossed and/or matte finished to provide a more cloth-like texture or appearance. The outer cover 26 can permit vapors to escape from the absorbent article 10, 110, 210, 310, 410 while preventing liquids from passing through. A suitable liquid impermeable, vapor permeable material can be composed of a microporous polymer film or a non-woven material which has been coated or otherwise treated to impart a desired level of liquid impermeability.

Bodyside Liner:

The bodyside liner 28 of the absorbent article 10, 110, 210, 310, 410 can overlay the absorbent body 34, 134, 234, 334, 434 and the outer cover 26 and can isolate the wearer's skin from liquid waste retained by the absorbent body 34, 134, 234, 334, 434. In various embodiments, a fluid transfer layer (not shown) can be positioned between the bodyside liner 28 and the absorbent body 34, 134, 234, 334, 434. In various embodiments, an acquisition layer (not shown) can be positioned between the bodyside liner 28 and the absorbent body 34, 134, 234, 334, 434 or a fluid transfer layer, if present. In various embodiments, the bodyside liner 28 can be bonded to the acquisition layer, or to the fluid transfer layer if no acquisition layer is present, via adhesive and/or by a point fusion bonding. The point fusion bonding may be selected from ultrasonic, thermal, pressure bonding, and combinations thereof.

In an embodiment, the bodyside liner 28 can extend beyond the absorbent body 34, 134, 234, 334, 434 and/or a fluid transfer layer, if present, and/or an acquisition layer, if present, and/or a spacer layer, if present, to overlay a portion of the outer cover 26 and can be bonded thereto by any method deemed suitable, such as, for example, by being bonded thereto by adhesive, to substantially enclose the absorbent body 34, 134, 234, 334, 434 between the outer cover 26 and the bodyside liner 28. The bodyside liner 28 may be narrower than the outer cover 26. However, in other embodiments, the bodyside liner 28 and the outer cover 26 may be of the same dimensions in width and length. In other embodiments, the bodyside liner 28 can be of greater width than the outer cover 26. It is also contemplated that the bodyside liner 28 may not extend beyond the absorbent body 34, 134, 234, 334, 434 and/or may not be secured to the outer cover 26. In some embodiments, the bodyside liner 28 can wrap at least a portion of the absorbent body 34, 134, 234, 334, 434. It is further contemplated that the bodyside liner 28 may be composed of more than one segment of material. The bodyside liner 28 can be of different shapes, including rectangular, hourglass, or any other shape. The bodyside liner 28 can be suitably compliant, soft feeling, and non-irritating to the wearer's skin and can be the same as or less hydrophilic than the absorbent body 34, 134, 234, 334, 434 to permit body exudates to readily penetrate through to the absorbent body 34, 134, 234, 334, 434 and provide a relatively dry surface to the wearer.

The bodyside liner 28 can be manufactured from a wide selection of materials, such as synthetic fibers (for example, polyester or polypropylene fibers), natural fibers (for example, wood or cotton fibers), a combination of natural and synthetic fibers, porous foams, reticulated foams, apertured plastic films, or the like. Examples of suitable materials include, but are not limited to, rayon, wood, cotton, polyester, polypropylene, polyethylene, nylon, or other heat-bondable fibers, polyolefins, such as, but not limited to, copolymers of polypropylene and polyethylene, linear low-density polyethylene, and aliphatic esters such as polylactic acid, finely perforated film webs, net materials, and the like, as well as combinations thereof.

Various woven and non-woven fabrics can be used for the bodyside liner 28. The bodyside liner 28 can include a woven fabric, a nonwoven fabric, a polymer film, a film-fabric laminate or the like, as well as combinations thereof. Examples of a nonwoven fabric can include spunbond fabric, meltblown fabric, coform fabric, carded web, bonded-carded web, bicomponent spunbond fabric, spunlace, or the like, as well as combinations thereof. The bodyside liner 28 need not be a unitary layer structure, and thus, can include more than one layer of fabrics, films, and/or webs, as well as combinations thereof. For example, the bodyside liner 28 can include a support layer and a projection layer that can be hydroentagled. The projection layer can include hollow projections, such as those disclosed in U.S. Patent Application Publication No. 2014/0121623 invented by Kirby, Scott S. C. et al.

For example, the bodyside liner 28 can be composed of a meltblown or spunbond web of polyolefin fibers. Alternatively, the bodyside liner 28 can be a bonded-carded web composed of natural and/or synthetic fibers. The bodyside liner 28 can be composed of a substantially hydrophobic material, and the hydrophobic material can, optionally, be treated with a surfactant or otherwise processed to impart a desired level of wettability and hydrophilicity. The surfactant can be applied by any conventional means, such as spraying, printing, brush coating or the like. The surfactant can be applied to the entire bodyside liner 28 or it can be selectively applied to particular sections of the bodyside liner 28.

In an embodiment, a bodyside liner 28 can be constructed of a non-woven bicomponent web. The non-woven bicomponent web can be a spunbonded bicomponent web, or a bonded-carded bicomponent web. An example of a bicomponent staple fiber includes a polyethylene/polypropylene bicomponent fiber. In this particular bicomponent fiber, the polypropylene forms the core and the polyethylene forms the sheath of the fiber. Fibers having other orientations, such as multi-lobe, side-by-side, end-to-end may be used without departing from the scope of this disclosure. In an embodiment, a bodyside liner 28 can be a spunbond substrate with a basis weight from about 10 or 12 to about 15 or 20 gsm. In an embodiment, a bodyside liner 28 can be a 12 gsm spunbond-meltblown-spunbond substrate having 10% meltblown content applied between the two spunbond layers.

Although the outer cover 26 and bodyside liner 28 can include elastomeric materials, it is contemplated that the outer cover 26 and the bodyside liner 28 can be composed of materials which are generally non-elastomeric. In an embodiment, the bodyside liner 28 can be stretchable, and more suitably elastic. In an embodiment, the bodyside liner 28 can be suitably stretchable and more suitably elastic in at least the lateral or circumferential direction of the absorbent article 10, 110, 210, 310, 410. In other aspects, the bodyside liner 28 can be stretchable, and more suitably elastic, in both the lateral and the longitudinal directions 32, 30, respectively.

Fastening System:

In an embodiment, the absorbent article 10, 110, 210, 310 can include a fastening system. The fastening system can include one or more back fasteners 91 and one or more front fasteners 92. The embodiments shown in FIGS. 1, 2, 7, 8, and 10 depict embodiments with one front fastener 92. Portions of the fastening system may be included in the front waist region 12, rear waist region 14, or both.

The fastening system can be configured to secure the absorbent article 10, 110, 210, 310 about the waist of the wearer in a fastened condition as shown in FIG. 1 and help maintain the absorbent article 10, 110, 210, 310 in place during use. In an embodiment, the back fasteners 91 can include one or more materials bonded together to form a composite ear as is known in the art. For example, the composite fastener may be composed of a stretch component 94, a nonwoven carrier or hook base 96, and a fastening component 98, as labeled in FIGS. 2 and 6. As shown in FIG. 5B, in some embodiments the waist containment member 54 can extend to back fasteners 91. In some embodiments, the waist containment member 54 can be directly coupled to the stretch component 94 of the back fasteners 91.

Figure 2:
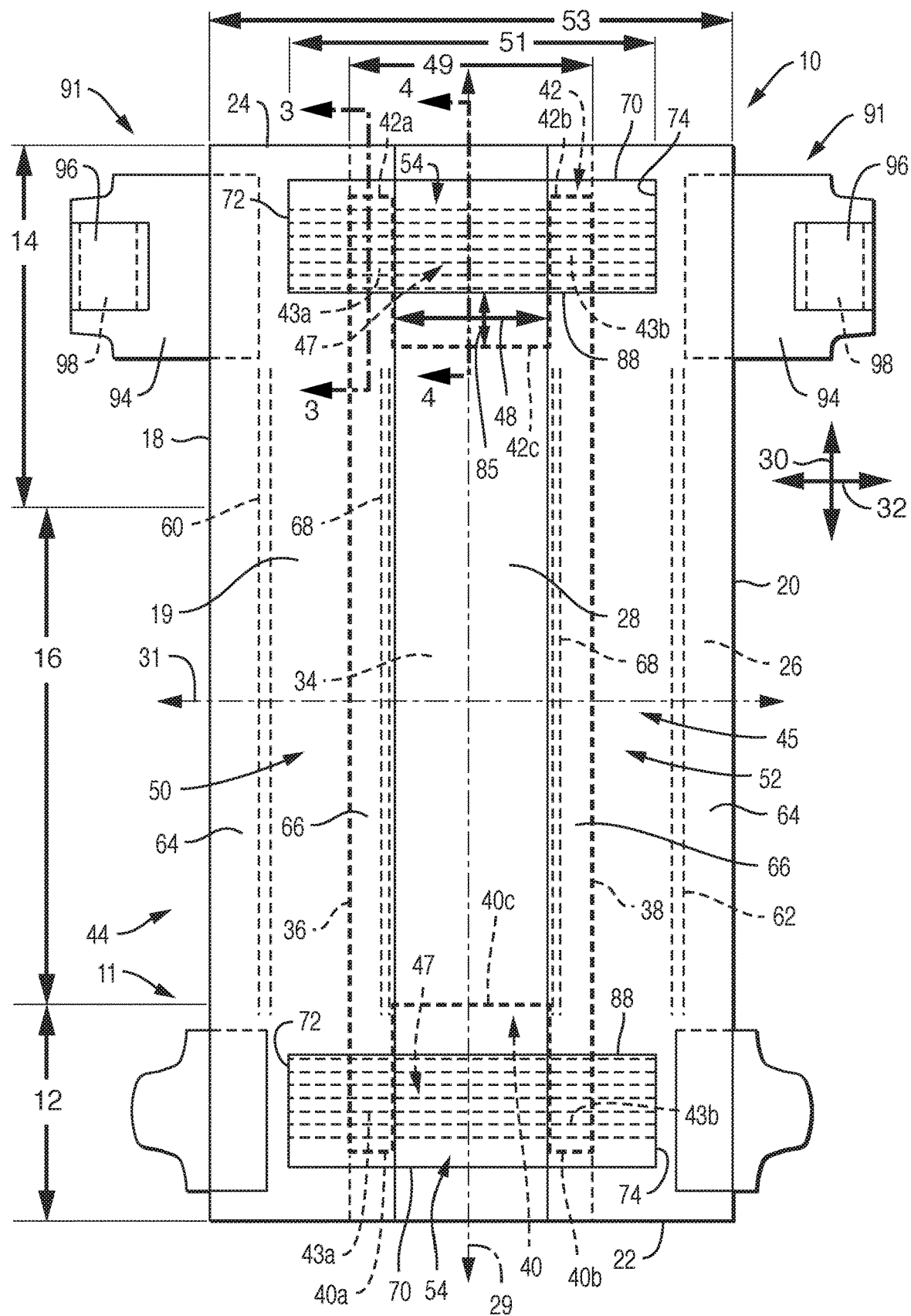
FIG. 2 is a top plan view of the absorbent article of FIG. 1 in a stretched, laid flat, unfastened condition.

Absorbent Body:

The absorbent body 34, 134, 234, 334, 434 of the respective embodiments of the absorbent articles 10, 110, 210, 310, 410 as described and illustrated herein can be suitably constructed to be generally compressible, conformable, pliable, non-irritating to the wearer's skin and capable of absorbing and retaining liquid body exudates. The absorbent body 34, 134, 234, 334, 434 can be manufactured in a wide variety of sizes and shapes (for example, rectangular, trapezoidal, T-shape, I-shape, hourglass shape, etc.) and from a wide variety of materials. As illustrated in FIG. 2, the absorbent body 34 can include longitudinal side edges 36, 38 opposite from one another and a first end edge 40 and a second end edge 42. The first end edge 40 can be opposite from the second end edge 42. The longitudinal side edges 36, 38 can extend between the first end edge 40 and the second end edge 42. Although the first end edge 40 is illustrated as being disposed in the front waist region 12 and the second end edge 42 is illustrated as being disposed in the rear waist region 14, the classification of "first" and "second" need not be synonymous with the "front" and "rear" waist regions 12, 14. For example, the first end edge 40 could be in the rear waist region 14.

The size and the absorbent capacity of the absorbent body 34, 134, 234, 334, 434 should be compatible with the size of the intended wearer (infants to adults) and the liquid loading imparted by the intended use of the absorbent article 10, 110, 210, 310, 410. The absorbent body 34, 134, 234, 334, 434 can have a length and width that can be less than or equal to the length and width of the absorbent article 10, 110, 210, 310, 410.

In an embodiment, the absorbent body 34, 134, 234, 334, 434 can be composed of a web material of hydrophilic fibers, cellulosic fibers (e.g., wood pulp fibers), natural fibers, synthetic fibers, woven or nonwoven sheets, scrim netting or other stabilizing structures, superabsorbent material, binder materials, surfactants, selected hydrophobic and hydrophilic materials, pigments, lotions, odor control agents or the like, as well as combinations thereof. In an embodiment, the absorbent body 34, 134, 234, 334, 434 can be a matrix of cellulosic fluff and superabsorbent material. In an embodiment, the absorbent body 34, 134, 234, 334, 434 may be constructed of a single layer of materials, or in the alternative, may be constructed of two or more layers of materials.

Various types of wettable, hydrophilic fibers can be used in the absorbent body 34, 134, 234, 334, 434. Examples of suitable fibers include natural fibers, cellulosic fibers, synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers, or composed of nonwettable thermoplastic polymers, such as polyolefin fibers which have been hydrophilized by suitable means. The fibers may be hydrophilized, for example, by treatment with a surfactant, treatment with silica, treatment with a material which has a suitable hydrophilic moiety and is not readily removed from the fiber, or by sheathing the nonwettable, hydrophobic fiber with a hydrophilic polymer during or after formation of the fiber. Suitable superabsorbent materials can be selected from natural, synthetic, and modified natural polymers and materials. The superabsorbent materials can be inorganic materials, such as silica gels, or organic compounds, such as cross-linked polymers. In an embodiment, the absorbent body 34, 134, 234, 334, 434 can be free of superabsorbent material.

If a spacer layer (not shown) is present, the absorbent body 34, 134, 234, 334, 434 can be disposed on the spacer layer and superposed over the outer cover 26. The spacer layer can be bonded to the outer cover 26, for example, by adhesive. In some embodiments, a spacer layer may not be present and the absorbent body 34, 134, 234, 334, 434 can directly contact the outer cover 26 and can be directly bonded to the outer cover 26. However, it is to be understood that the absorbent body 34, 134, 234, 334, 434 may be in contact with, and not bonded with, the outer cover 26 and remain within the scope of this disclosure. In an embodiment, the outer cover 26 can be composed of a single layer and the absorbent body 34, 134, 234, 334, 434 can be in contact with the singer layer of the outer cover 26. In some embodiments, at least a portion of a layer, such as but not limited to, a fluid transfer layer (not shown) and/or a spacer layer, can be positioned between the absorbent body 34, 134, 234, 334, 434 and the outer cover 26. The absorbent body 34, 134, 234, 334, 434 can be bonded to the fluid transfer layer and/or the spacer layer if present.

In some embodiments, such as in the absorbent body 34 depicted in FIGS. 2-6, the second end edge 42 of the absorbent body 34 can include a first portion 42a, a second portion 42b, and an intermediate portion 42c. The intermediate portion 42c can be disposed between the first portion 42a and the second portion 42b. As illustrated in FIG. 2, the absorbent body 34 can include a first section 43a near the second end edge 42 and a second section 43b near the second end edge 42. The first section 43a can include the first portion 42a of the second end edge 42 of the absorbent body 34. The second section 43a can include the second portion 42b of the second end edge 42 of the absorbent body 34. In the embodiment illustrated in FIG. 2, the absorbent body 34 can be configured to have an area 47 with no absorbent material laterally between the first section 43a and the second section 43b.

As illustrated in FIG. 2, the first portion 42a and the second portion 42b of the second end edge 42 of the absorbent body 34 can be disposed under the waist containment member 54, but the intermediate portion 42c can be configured such that is not disposed under the waist containment member 54, as will be discussed in further detail below. As discussed herein, a portion or component being disposed "under" another component or portion refers to the juxtaposition of components in the plane created by the longitudinal direction 30 and the lateral direction 32 when the absorbent article 10, 110, 210, 310, 410 is in the stretched, laid-flat configuration and when viewing the absorbent article 10, 110, 210, 310, 410 from the body facing surface 19 of the chassis 11, such as illustrated in FIGS. 2, 7, 8, 10, and 12. For example, the first portion 42a of the second end edge 42 of the absorbent body 34 is disposed "under" the waist containment member 54 because at least a portion of the waist containment member 54 overlaps with or is superposed over the first portion 42a of the second end edge 42 of the absorbent body 34 of FIG. 2. In contrast, the intermediate portion 42c of the second end edge 42 of the absorbent body 34 is not disposed "under" the waist containment member 54 because the waist containment member 54 does not overlap with nor is superposed over the intermediate portion 42c of the second end edge 42 of the absorbent body 34 of FIG. 2. In other words, a gap 85 is created between the intermediate portion 42c of the second end edge 42 of the absorbent body 34 and the lower lateral edge 88 of the waist containment member 54. The advantages and benefits of such a configuration are described in further detail below.

The absorbent article 410 and absorbent body 434 in the absorbent article 410 depicted in FIG. 12 provides a similar example of a first portion 442a, second portion 442b, and intermediate portion 442c of the second end edge 442 of the absorbent body 434 as depicted in FIG. 2. As illustrated in FIGS. 2 and 12, the second end edge 42, 442 can be linear, arcuate, or curved. Likewise, portions 42a, 42b, 42c of the second end edge 42 of the absorbent body 34 of FIG. 2 are linear segments whereas portions 442a, 442b, 442c of the second end edge 442 of the absorbent body 434 of FIG. 12 are arcuate in shape.

In some embodiments, the first end edge 40 of the absorbent body 34 can be configured in a similar manner to the second end edge 42 of the absorbent body 34 described above. For example, the first end edge 40 illustrated in FIG. 2 includes a first portion 40a, a second portion 40b, and an intermediate portion 40c, where the intermediate portion 40c is between the first portion 40a and the second portion 40b and the first portion 40a and the second portion 40b are disposed under a waist containment member 54, but the intermediate portion 40c is not disposed under the waist containment member 54.

Figure 3:
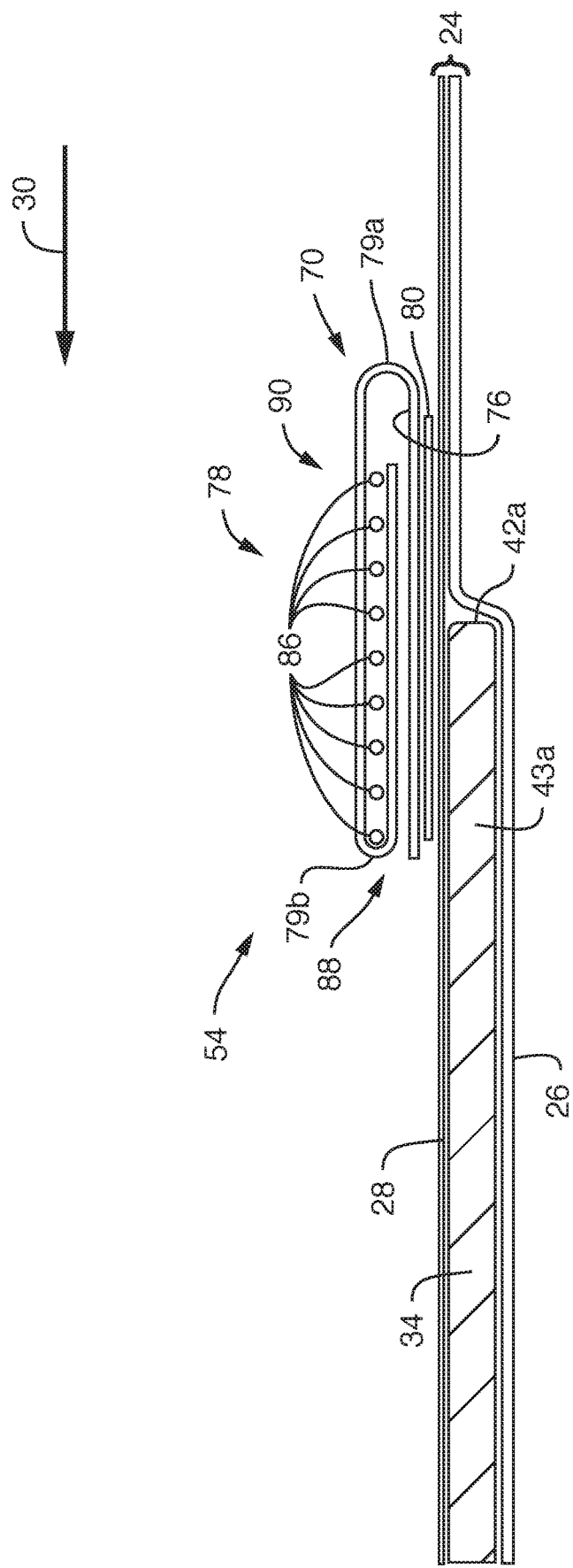
FIG. 3 is a cross-sectional view taken along line 3-3 from FIG. 2.
Figure 4:
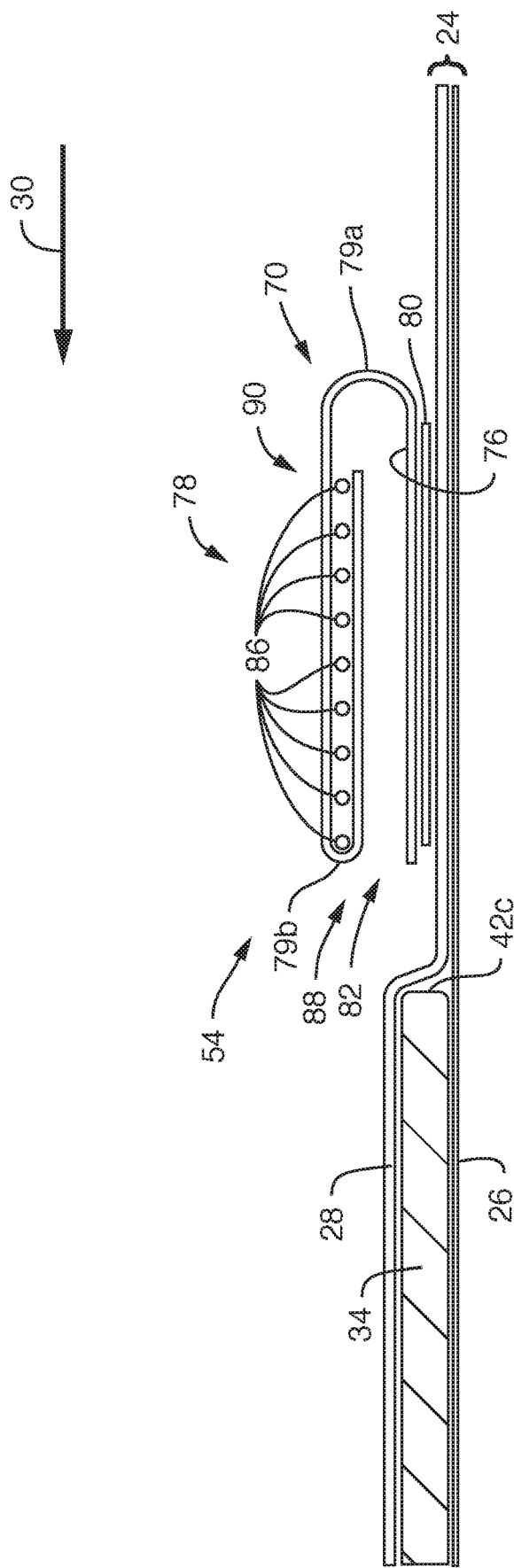
FIG. 4 is a cross-sectional view taken along line 4-4 from FIG. 2.

FIGS. 3 and 4 provide two cross-sectional views of the absorbent body 34 of FIG. 2. FIG. 3 depicts a cross-sectional view through the first section 43a of the absorbent body 34 near the second end edge 42 and through the first portion 42a of the second end edge 42. FIG. 4 depicts a cross-sectional view through the intermediate portion 42c of the second end edge 42 of the absorbent body 34. As illustrated in FIG. 3 and as discussed above, the first section 43a and the first portion 42a of the second end edge 42 of the absorbent body 34 are disposed under the waist containment member 54. A similar view would be depicted if a cross-section was taken through the second section 43b of the absorbent body 34 and the second portion 42b of the second end edge 42 of the absorbent body 34. As shown in FIG. 4, however, the intermediate portion 42c of the second end edge 42 of the absorbent body 34 is not disposed under the waist containment member 54, and thus, a gap 85 is created between the intermediate portion 42c of the second end edge 42 of the absorbent body 34 and lower lateral edge 88 of the waist containment member 54.

FIGS. 5 and 6 provide similar cross-sectional views to FIGS. 3 and 4, respectively, except where the absorbent article 10 is being worn by a wearer 101 over the wearer's buttocks 103 and lower back 105. In FIG. 5, the cross-section is being taken through the first section 43a of the absorbent body 34 and through the first portion 42a of the second end edge 42 of the absorbent body. In FIG. 6, the cross-section is being taken through the intermediate portion 42c of the second end edge 42 of the absorbent body 34.

As shown in FIG. 5, the waist containment member 54 is compressed against the wearer's skin at their lower back 105 and the first section 43a of the absorbent body 34 compresses the proximal portion 76 of the waist containment member 54 against the distal portion 78 of the waist containment member 54, rendering it challenging for exudates to enter the containment pocket 82 created by the waist containment member 54. A similar phenomena would be viewed if a cross-section would be taken through the second section 43b of the absorbent body 34 and the second portion 42b of the second end edge 42 of the absorbent body 34.

However, FIG. 6 illustrates that the waist containment member 54 is not compressed tightly against the wearer's skin at their lower back 105 when viewed at the cross-section through the intermediate portion 42c of the second end edge 42 of the absorbent body 34. Instead, the distal portion 78 of the waist containment member 54 can be disposed against the wearer's skin, but the proximal portion 76 can be kept away from compressing against the distal portion 78 of the waist containment member 54 to provide a better entrance, or improved access, for exudates to the containment pocket 82 created by the waist containment member 54. In addition to the improvement of access of exudates to enter the containment pocket 82, the configuration of the absorbent body 34 can also provide the benefit of increased void volume in the containment pocket 82.

In embodiments where the absorbent article 10, 110, 210, 310 includes back fasteners 91 with a stretch component 94, the waist containment member 54 can be disposed to be longitudinally aligned with the stretch component 94 of the back fasteners 91. This longitudinal alignment is of particular relevance to help improve access to the containment pocket 82 of the waist containment member 54 as described above. As the stretch components 94 of the back fasteners 91 are stretched in opposite directions (for donning the absorbent article 10, 110, 210, 310 as well as in the fastened configuration), the stretch components 94 can apply a tensioning force to the waist containment member 54. This tensioning force can force the distal portion 78 of the waist containment member 54 towards the body facing surface 19 of the chassis 11 (e.g., the bodyside liner 28), such as shown in FIG. 6. However, by having the first portion 42a and the second portion 42b be disposed under the waist containment member 54, but having the intermediate portion 42c not be disposed under the waist containment member 54, the containment pocket 82 can have improved access near the intermediate portion 42c of the absorbent body 34, as well as having improved void volume overall.

In some embodiments, the lateral width 48 of the intermediate section 42c can be at least 25% of the lateral width 49 of the second end edge 42 of the absorbent body 34, more preferably at least 30% of the lateral width 49 of the second end edge 42 of the absorbent body 34, and even more preferably at least 40% of the lateral width 49 of the second end edge 42 of the absorbent body 34. In some embodiments, the lateral width 48 of the intermediate section 42c can be at least 50% of the lateral width 49 of the second end edge 42 of the absorbent body 34. As shown in FIG. 2, the lateral width 48 of the intermediate section 42c and the lateral width 49 of the second end edge 42 is measured in the lateral direction 32 when the absorbent article 10 is in the stretched, laid flat configuration.

In some embodiments, such as in the embodiment of the absorbent article 110 depicted in FIG. 7, the absorbent body 134 can be configured such that the second end edge 142 includes at least two intermediate sections 142c. For example, the absorbent body 134 includes four intermediate section 142c that are not disposed under the waist containment member 54 in FIG. 7. Of course it is contemplated that the absorbent body 34 can be configured such that the second end edge 142 could include other amounts of intermediate sections 142c, such as two, three, or five or more intermediate sections 142c that are not disposed under the waist containment member 54.

The intermediate sections 142c can each provide improved access to the containment pocket 182 as well as increased void volume for the containment pocket 182, as discussed above. The areas 147 of no absorbent material relating to the intermediate sections 142c of the absorbent body 134 can create grooves or channels and are shown as longitudinal-oriented rectangles in FIG. 7, however, it can be appreciated that these areas could be of any suitable shape and/or size. The combined lateral width (not labeled for purposes of clarity) of the intermediate sections 142c can be calculated by adding together the lateral width of each of the intermediate sections 142c for the second end edge 142 of the absorbent body 134, as measured in the lateral direction 32 when the absorbent article 110 is in the stretched, laid flat configuration. The combined lateral width of the intermediate sections 142c can be at least 25% of the lateral width 149 of the second end edge 142 of the absorbent body 134, more preferably at least 30% of the lateral width 149 of the second end edge 142 of the absorbent body 134, and even more preferably at least 40% of the lateral width 149 of the second end edge 142 of the absorbent body 134. In some embodiments, the combined lateral width of the intermediate sections 142c can be at least 50% of the lateral width 149 of the second end edge 142 of the absorbent body 134.

Turning now to FIGS. 8 and 9, another embodiment of an absorbent article 210 is illustrated. The absorbent article 210 can include an absorbent body 234 that can include a first section 243a near the second end edge 242 having a first thickness 246a. The absorbent body 234 can also include a second section 243b near the second end edge 242 having a second thickness 246b. In some embodiments, the first thickness 246a can be substantially equal to the second thickness 246b. The absorbent body 234 can include an intermediate section 243c disposed between the first section 243a and the second section 243b. The intermediate section 243c can include a thickness 246c that is less than the first thickness 246a and that is less than the second thickness 246b. The first thickness 246a and the second thickness 246b are labeled in FIG. 9 as the thickness of the absorbent body 234 longitudinally adjacent to the intermediate section 243c, as the first thickness 246a and the second thickness 246b can be substantially equal to the thickness of the absorbent body longitudinally below the intermediate section 243c. In some embodiments, the thickness 246c of the intermediate section 243c can be less than 75% of the thickness 246a of the first section 243a and less than 75% of the thickness 246b of the second section 243b. In a preferred embodiment, the thickness 246c of the intermediate section 243c can be less than 50% of the thickness 246a of the first section 243a and less than 50% of the thickness 246b of the second section 243b.

The intermediate section 243c of reduced thickness can be provided in a variety of ways. In one example, the intermediate section 243c can be provided by embossing an absorbent body 234 in the intermediate section 243c, but not embossing the first section 243a or the second section 243b. Of course, it is contemplated that the intermediate section 243c having a reduced thickness can be provided via other methods and still be within the scope of this disclosure.

In some embodiments, the absorbent body 234 can include a bridge section 243d near the second end edge 242 that spans between the first section 243a and the second section 243b. The bridge section 243d can include a thickness (not labeled in FIG. 9 for purposes of clarity) that is greater than the thickness 246c of the intermediate section 243c. In some embodiments, the thickness of the bridge section 243d can be substantially equal to the first thickness 246a and/or can be substantially equal to the second thickness 246b. Additionally, the intermediate section 243c can include a lower edge 243e that is not disposed under the waist containment member 54, as illustrated in FIGS. 8 and 9.

As illustrated in FIG. 8, at least a portion of the intermediate section 243c can be disposed under the waist containment member 54. In some embodiments, the lower edge 243e of the intermediate section 243c can be disposed such that the lower edge 243e is not disposed under the waist containment member 54. By having reduced thickness 246c of the absorbent body 34 in the intermediate section 243c as compared to the thickness 246a of the first section 243a and the thickness 246b of the second section 243b, the waist containment member 54 can have increased void volume. Additionally, by having the lower edge 243e of the intermediate section 243c not disposed under the waist containment member 54 can provide for the benefit of improved access for exudates into the containment pocket 82, as discussed above with respect to configurations of the absorbent bodies 34, 134 discussed above and illustrated in FIGS. 2 and 7, respectively.

Another alternative embodiment of an absorbent article 310 including an absorbent body 334 and a waist containment member 54 is illustrated in FIG. 10. The embodiment in FIG. 10 is similar to the embodiment illustrated in FIGS. 8 and 9, however, the absorbent body 334 in FIG. 10 includes a plurality of intermediate sections 343*c*, or in other words, at least two intermediate sections 343*c*. The absorbent body 334 illustrated in FIG. 10 includes four intermediate sections 343*c*, but it is contemplated that the absorbent body 334 could include other numbers of intermediate sections 343*c* other than four intermediate sections 343*c*. Additionally, although the intermediate sections 343*c* are shown as longitudinal-oriented rectangles in FIG. 10, it can be appreciated that the intermediate sections 343*c* could be of any suitable shape and/or size.

The intermediate sections 343*c* can include a thickness that is less than the first thickness of the first section 343*a* of the absorbent body 334 near the second end edge 342. The intermediate sections 343*c* can include a thickness that is less than the second thickness of the second section 343*b* of the absorbent body 334 near the second end edge 342. In one embodiment, the thickness of each of the intermediate sections 343*c* can be substantially the same. In some embodiments, the thickness of each of the intermediate sections 343*c* can be less than 75% of the thickness of the first section 343*a* and less than 75% of the thickness of the second section 343*b*. In a preferred embodiment, the thickness of each of the intermediate sections 343*c* can be less than 50% of the thickness of the first section 343*a* and less than 50% of the thickness of the second section 343*b*. The absorbent body 334 can also include a bridge section 343*d*. The bridge section 343*d* can include a thickness that is substantially equal to the first thickness of the first section 343*a* and/or substantially equal to the second thickness of the second section 343*b*. Although a cross-sectional view is not shown for the embodiment for FIG. 10 through an intermediate section 343*c*, the thicknesses of the intermediate sections 343*c*, the first section 343*a*, the second section 343*b*, and the bridge section 343*d* could appear similar to the cross-sectional view through the intermediate section 243*c* of the absorbent body 234 illustrated in FIG. 9. The intermediate sections 343*c* can each provide similar benefits as noted above for the intermediate section 243*c* of absorbent body 234 discussed above and illustrated in FIGS. 8 and 9.

Containment Flaps:

In an embodiment, the absorbent article 10, 110, 210, 310, 410 can include a pair of containment flaps 50, 52. The containment flaps 50, 52 can be formed separately from the absorbent chassis 11 and attached to the chassis 11 or can be formed integral to the chassis 11. In some embodiments, the containment flaps 50, 52 can be secured to the chassis 11 of the absorbent article 10, 110, 210, 310, 410 in a generally parallel, spaced relation with each other laterally inward of the leg openings to provide a barrier against the flow of body exudates. One containment flap 50 can be on a first side of the longitudinal axis 29 and the other containment flap 52 can be on a second side of the longitudinal axis 29. In an embodiment, the containment flaps 50, 52 can extend generally in a longitudinal direction 30 from the front waist region 12 of the absorbent article 10, 110, 210, 310 through the crotch region 16 to the rear waist region 14 of the absorbent article 10, 110, 210, 310. In some embodiments, the containment flaps 50, 52 can extend in a direction substantially parallel to the longitudinal axis 29 of the absorbent article 10, 110, 210, 310, 410, however, in other embodiments, the containment flaps 50, 52 can be curved, as is known in the art. In other embodiments, such as the absorbent article 210 in FIGS. 11 and 12, the containment flaps 50, 52 can be disposed on the absorbent panel 17 in the crotch region 16.

In embodiments where the containment flaps 50, 52 are coupled to the chassis 11, the containment flaps 50, 52 can be bonded to the bodyside liner 28, the outer cover 26, or a spacer layer (not shown) if present with a barrier adhesive, as is known by one of ordinary skill in the art. Of course, the containment flaps 50, 52 can be bonded to other components of the chassis 11 and can be bonded with other suitable means other than a barrier adhesive. The containment flaps 50, 52 can be constructed of a fibrous material which can be similar to the material forming the bodyside liner 28. Other conventional materials, such as polymer films, can also be employed.

The containment flaps 50, 52 can each include a base portion 64, a projection portion 66, and one or more flap elastic members 68 (as labeled in FIGS. 2 and 12). The base portion 64 can be bonded to the chassis 11, for example, to the bodyside liner 28 or the outer cover 26 as mentioned above. The projection portion 66 can extend away from the body facing surface 19 of the chassis 11 at least in the crotch region 16 when the absorbent article 10, 110, 210, 310, 410 is in a relaxed configuration. Suitable elastic materials for the flap elastic members 68 can include sheets, strands or ribbons of natural rubber, synthetic rubber, or thermoplastic elastomeric materials. Of course, while two elastic members 68 are shown in each containment flap 50, 52, it is contemplated that the containment flaps 50, 52 can be configured with one or three or more elastic members 68. Alternatively or additionally, the containment flaps 50, 52 can be composed of a material exhibiting elastic properties itself. It is contemplated that the containment flaps 50, 52 can be of various configurations and shapes, and can be constructed by various methods, as known by one of ordinary skill in the art.

Leg Elastics:

Leg elastic members 60, 62 can be secured to the outer cover 26, such as by being bonded thereto by laminate adhesive, generally laterally inward of the longitudinal side edges, 18 and 20, of the absorbent article 10, 110, 210, 310, 410. The leg elastic members 60, 62 can form elasticized leg cuffs that further help to contain body exudates. In an embodiment, the leg elastic members 60, 62 may be disposed between inner and outer layers (not shown) of the outer cover 26 or between other layers of the absorbent article 10, 110, 210, 310, 410, for example, between the base portion 64 of each containment flap 50, 52 and the bodyside liner 28, between the base portion 64 of each containment flap 50, 52 and the outer cover 26, or between the bodyside liner 28 and the outer cover 26. The leg elastic members 60, 62 can be one or more elastic components near each longitudinal side edge 18, 20. For example, the leg elastic members 60, 62 as illustrated herein each include two elastic strands. A wide variety of elastic materials may be used for the leg elastic members 60, 62. Suitable elastic materials can include sheets, strands or ribbons of natural rubber, synthetic rubber, or thermoplastic elastomeric materials. The elastic materials can be stretched and secured to a substrate, secured to a gathered substrate, or secured to a substrate and then elasticized or shrunk, for example, with the application of heat, such that the elastic retractive forces are imparted to the substrate. Additionally, it is contemplated that the leg elastic members 60, 62 can be formed with the containment flaps 50, 52, and then attached to the chassis 11 in some embodiments. Of course, the leg elastic members 60, 62 can be omitted from the absorbent article 10, 110, 210, 310, 410 without departing from the scope of this disclosure.

Waist Containment Member:

In an embodiment, the absorbent article 10, 110, 210, 310, 410 can have one or more waist containment members 54. As will be discussed in more detail below, the waist containment member 54 can help contain and/or absorb body exudates, especially low viscosity fecal matter, and as such, can be preferred to be in the rear waist region 14. In some embodiments, such as illustrated in FIG. 2, an absorbent article 10 can have a waist containment member 54 disposed in the front waist region 12. A waist containment member 54 in the front waist region 12 can help contain and/or absorb body exudates, such as urine, in the front waist region 12. Although not as prevalent as in the rear waist region 14, in some circumstances, fecal material may also spread to the front waist region 12, and thus, a waist containment member 54 disposed in the front waist region 12 can help contain and/or absorb body exudates as well. In some embodiments, such as the absorbent article 10 depicted in FIG. 2, a waist containment member 54 can be in both the rear waist region 14 and the front waist region 12.

The waist containment member 54 can be disposed on the body facing surface 45 of the absorbent assembly 44. In some embodiments, such as in embodiments illustrated in FIGS. 1-10, the waist containment member 54 can be disposed on the body facing surface 56 of the bodyside liner 28. However, in some embodiments, such as the absorbent article 410 in FIG. 12, the waist containment member 54 can be disposed on a body facing surface 58 of the rear waist panel 15.

The waist containment member 54 can include a first longitudinal side edge 72 and a second longitudinal side edge 74 (labeled in FIGS. 2 and 12). The first longitudinal side edge 72 can be opposite from the second longitudinal side edge 74. The distance between the first longitudinal side edge 72 and the second longitudinal side edge 74 can define a width 51 of the waist containment member 54 in the lateral direction 32, as shown in FIG. 2. It can be appreciated that in some embodiments, the first longitudinal side edge 72 can substantially align with the first longitudinal side edge 18 of the absorbent article 10, 110, 210, 310, 410. Similarly, in some embodiments, the second longitudinal side edge 74 can align with the second longitudinal side edge 20 of the absorbent article 10, 110, 210, 310, 410.

The waist containment member 54 can also include an upper lateral edge 70 and a lower lateral edge 88 (as labeled in FIGS. 2 and 12). The upper lateral edge 70 can be opposite from the lower lateral edge 88. As illustrated in FIGS. 3-6 and 9, the waist containment member 54 can also include a proximal portion 76 and a distal portion 78. The proximal portion 76 can be coupled to the body facing surface 19 of chassis 11 (e.g., the body facing surface 45 of the absorbent assembly 44 or the body facing surface 56 of the bodyside liner 28) whereas the distal portion 78 of the waist containment member 54 can be free to move with respect to the chassis 11 and the absorbent assembly 44 when the absorbent article 10, 110, 210, 310, 410 is in the relaxed configuration.

In some preferred embodiments, the waist containment member 54 can include a fold 79a that can separate the proximal portion 76 from the distal portion 78 of the waist containment member 54. As used in this context, the fold 79a separates the proximal portion 76 from the distal portion 78 in that the fold 79a defines a transition between the proximal portion 76 and the distal portion 78. However, it is contemplated that the waist containment member 54 need not include a fold 79a to separate the proximal portion 76 from the distal portion 78. It is contemplated that the present disclosure includes a waist containment member 54 that is not folded in such a C-shape fashion as illustrated in FIGS. 3-6 and 9. For example, it is intended that a waist containment member 54 having a proximal portion 76 that is not under the distal portion 78 is within the scope of this disclosure.

The proximal portion 76 can be coupled to the body facing surface 19 of the chassis 11 with an adhesive 80 (as labeled in FIGS. 3, 4, and 9), and in some embodiments, the proximal portion 76 can be coupled to the body facing surface 45 of the absorbent assembly 44. In some embodiments, such as in embodiments illustrated in FIGS. 2-10, the proximal portion 76 of the waist containment member 54 can be coupled to the body facing surface 56 of the bodyside liner 28. However, in some embodiments, such as the absorbent article 410 in FIG. 12, the proximal portion 76 of the waist containment member 54 can be coupled to the body facing surface 58 of the rear waist panel 15. The proximal portion 76 can be coupled to the body facing surface 45 of the absorbent assembly 44 with adhesive 80 along the entire length of the proximal portion 76 in the longitudinal direction 30, however, it can be contemplated that only a portion of the proximal portion 76 in the longitudinal direction 30 is coupled to the body facing surface 45 of the absorbent assembly 44. Of course, it is contemplated that the proximal portion 76 of the waist containment member 54 can be coupled to the body facing surface 19 of the chassis 11 or the body facing surface 45 of the absorbent assembly 44 by means other than an adhesive 80, such as by pressure bonding, ultrasonic bonding, thermal bonding, and combinations thereof. In preferred embodiments, the proximal portion 76 is coupled to the body facing surface 19 of the chassis 11 in the lateral direction 32 in a continuous fashion, as opposed to an intermittent fashion, such that a barrier to body exudates is formed between the proximal portion 76 and the body facing surface 19 of the chassis 11.

As illustrated in the embodiment depicted in FIGS. 3 and 4, the proximal portion 76 of the waist containment member 54 can include a longitudinal length measured in the longitudinal direction 30 that is substantially the same as a longitudinal length of the distal portion 78 of the waist containment member 54. In some embodiments, such as the embodiment illustrated in FIG. 9, the proximal portion 76 of the waist containment member 54 can include a longitudinal length measured in the longitudinal direction 30 that is less than a longitudinal length of the distal portion 78 of the waist containment member 54. Although not depicted, it is contemplated that the longitudinal length of the proximal portion 76 can be larger than the longitudinal length of the distal portion 78 of the waist containment member 54. For purposes herein, the longitudinal length of the proximal portion 76 and the longitudinal length of the distal portion 78 of the waist containment member 54 are measured when the absorbent article 10, 110, 210, 310, 410 is in the stretched, laid flat configuration.

As illustrated in FIG. 6, because the distal portion 78 of the waist containment member 54 can freely move with respect to the absorbent assembly 44 when the absorbent article 10 is in the relaxed configuration, the distal portion 78 can help provide the containment pocket 82 when the absorbent article 10 is in the relaxed configuration. The containment pocket 82 can help provide a barrier to contain and/or can help absorb body exudates. The containment pocket 82 can be especially beneficial for containing and/or absorbing low viscosity fecal matter, which can be prevalent in younger children. To help prevent lateral flow of body exudates that are contained by the containment pocket 82 of the waist containment member 54, the distal portion 78 of the waist containment member 54 can be bonded to the proximal portion 76 of the waist containment member 54 and/or the body facing surface 19 of the chassis 11 near the first and second longitudinal side edges 72, 74, respectively.

In some embodiments, the width 51 of the waist containment member 54 in the lateral direction 32 as compared to the width 53 of the chassis 11 (as labeled in FIG. 2) can have a ratio of about 0.85 to about 1.00. In some embodiments, the width 51 of the waist containment member 54 in the lateral direction 32 as compared to the width 53 of the chassis 11 can have a ratio of about 0.87 to about 1.00. And in other embodiments, the width 51 of the waist containment member 54 in the lateral direction 32 as compared to the width 53 of the chassis 11 can have a ratio of about 0.90 to about 1.00. For purposes herein, the width 53 of the chassis 11 for use in this ratio is the width of the chassis 11 in the waist region in which the waist containment member 54 is disposed and both width measurements are taken in a direction parallel to the lateral direction 32. Additionally, the width 51 of the waist containment member 54 in the lateral direction 32 and the width 53 of the chassis 11 as discussed for the ratios herein are to be measured when the absorbent article 10, 110, 210, 310, 410 is in the stretched, laid flat configuration.

In preferred embodiments, the waist containment member 54 can include at least one elastic member 86. In some embodiments, the waist containment member 54 can include multiple elastic members 86, such as nine elastic members 86 (as labeled in FIGS. 3, 4, and 9). Of course, it is contemplated that the waist containment member 54 can include other amounts of elastic members 86, or not include elastic members 86 at all. In some embodiments, the elastic members 86 can be spaced evenly in the longitudinal direction 30 in the distal portion 78 of the waist containment member 54. The elastic member 86 can span substantially from the first longitudinal side edge 72 to the second longitudinal side edge 74 of the waist containment member 54. The elastic member 86 can be disposed in the distal portion 78 of the waist containment member 54, and preferably, is located near a free edge 88 of the distal portion 78 of the waist containment member 54. As labeled in FIGS. 3, 4, and 9, in some preferred embodiments, the elastic member(s) 86 can be disposed within a laminate portion 90 of the distal portion 78 of the waist containment member 54 to aid in containing the elastic member(s) 86. The laminate portion 90 can be disposed near the free edge 88 of the distal portion 78 of the waist containment member 54 and, in some embodiments, can be formed by a fold 79b in the distal portion 78 at the lower lateral edge 88.

A wide variety of elastic materials may be used for the elastic member(s) 86 in the waist containment member 54. Suitable elastic materials can include sheets, strands or ribbons of natural rubber, synthetic rubber, elastic foams, or thermoplastic elastomeric materials (e.g., films). The elastic materials can be stretched and secured to a substrate forming the waist containment member 54, secured to a gathered substrate, or secured to a substrate and then elasticized or shrunk, for example, with the application of heat, such that the elastic retractive forces are imparted to the substrate forming the waist containment member 54.

The waist containment member 54 can be disposed to be coupled to the chassis 11 by being placed either over the containment flaps 50, 52, as depicted in the embodiments illustrated and described herein. However, it is also contemplated that the waist containment member 54 can be disposed to be coupled to the chassis 11 by being placed under the containment flaps 50, 52 as well.

The waist containment member 54 can be comprised of a variety of materials. In a preferred embodiment, the waist containment member 54 can be comprised of a spunbond-meltblown-spunbond ("SMS") material. However it is contemplated that the waist containment member 54 can be comprised of other materials including, but not limited to, a spunbond-film-spunbond ("SFS"), a bonded carded web ("BCW"), or any non-woven material. In some embodiments, the waist containment member 54 can be comprised of a laminate of more than one of these exemplary materials, or other materials. In some embodiments, the waist containment member 54 can be comprised of a liquid impermeable material. In some embodiments, the waist containment member 54 can be comprised of a material coated with a hydrophobic coating. The basis weight of the material forming the waist containment member 54 can vary, however, in a preferred embodiment, the basis weight can be between about 8 gsm to about 120 gsm, not including the elastic members 86 in the waist containment member 54. More preferably, the basis weight of the material comprising the waist containment member 54 can be between about 10 gsm to about 40 gsm, and even more preferably, between about 15 gsm to about 25 gsm.

As discussed above, the waist containment member 54 and absorbent body 34, 134, 234, 334, 434 can be configured to provide improved access to the containment pocket 82 of the waist containment member 54. In some embodiments, the absorbent body 34, 134, 234, 334, 434 can be configured to provide increased void volume for the containment pocket 82. The additional void volume can provide increased storage retention of exudates that are contained within the containment pocket 82.

Embodiments

Embodiment 1: An absorbent article comprising: a chassis including a body facing surface; a waist containment member disposed on the body facing surface of the chassis, the waist containment member comprising: a first longitudinal side edge and a second longitudinal side edge, the second longitudinal side edge being opposite from the first longitudinal side edge; an upper lateral edge and a lower lateral edge, the upper lateral edge being opposite from the lower lateral edge; a proximal portion being coupled to the body facing surface of the chassis; and a distal portion being free to move with respect to the chassis when the absorbent article is in the relaxed configuration to provide a pocket for exudates; and an absorbent body including a first end edge, a second end edge, and a pair of opposing longitudinal edges that extend between the first end edge and the second end edge, the first end edge of the absorbent body including a first portion, a second portion, and an intermediate portion, the first portion and the second portion each being disposed under waist containment member and the intermediate portion not being disposed under the waist containment member.

Embodiment 2: The absorbent article of embodiment 1, wherein a fold separates the proximal portion from the distal portion of the waist containment member.

Embodiment 3: The absorbent article of any one of the preceding embodiments, wherein the absorbent body includes at least two intermediate portions, wherein the at least two intermediate portions are not disposed under the waist containment member.

Embodiment 4: The absorbent article of embodiment 1 or embodiment 2, wherein the lateral width of the intermediate portion is at least 25% of a lateral width of the first end edge of the absorbent body.

Embodiment 5: The absorbent article of embodiment 1, wherein a combined width of the at least two intermediate portions is at least 25% of a lateral width of the first end edge of the absorbent body.

Embodiment 6: The absorbent article of any one of the preceding embodiments, wherein the waist containment member includes at least one elastic member.

Embodiment 7: The absorbent article of any one of the preceding embodiments, wherein the absorbent article further comprises: a fastening system including a pair of back fasteners disposed on opposite side edges of the absorbent article, the pair of back fasteners each including a stretch component, the waist containment member being longitudinally aligned with the stretch component of each back fastener.

Embodiment 8: The absorbent article of any one of the preceding embodiments, wherein the absorbent article includes a front waist region, a rear waist region, and a crotch region, the waist containment member being disposed in the rear waist region.

Embodiment 9: An absorbent article comprising: a chassis including a body facing surface; a waist containment member disposed on the body facing surface of the chassis, the waist containment member comprising: a first longitudinal side edge and a second longitudinal side edge, the second longitudinal side edge being opposite from the first longitudinal side edge; an upper lateral edge and a lower lateral edge, the upper lateral edge being opposite from the lower lateral edge; a proximal portion being coupled to the body facing surface of the chassis; and a distal portion being free to move with respect to the chassis when the absorbent article is in the relaxed configuration to provide a pocket for exudates; and an absorbent body comprising: a first end edge and a second end edge; a pair of opposing longitudinal edges that extend between the first end edge and the second end edge; a first section having a first thickness; a second section having a second thickness, the first section and the second section each at least partially disposed under the waist containment member; and an intermediate section between the first section and the second section, a thickness of the intermediate section being less than the first thickness and less than the second thickness, at least a portion of the intermediate section being disposed under the waist containment member.

Embodiment 10: The absorbent article of embodiment 9, wherein the intermediate section includes a lower edge, and the lower edge of the intermediate section is not disposed under the waist containment member.

Embodiment 11: The absorbent article of embodiment 9 or embodiment 10, wherein the first thickness is substantially equal to the second thickness.

Embodiment 12: The absorbent article of any one of embodiments 9-11, wherein the thickness of the intermediate section is less than 75% of the first thickness and less than 75% of the second thickness.

Embodiment 13: The absorbent article of any one of embodiments 9-12, wherein the absorbent body includes at least two intermediate sections wherein a thickness of each of the at least two intermediate sections is less than the first thickness and less than the second thickness.

Embodiment 14: The absorbent article of any one of embodiments 9-13, wherein a fold separates the proximal portion from the distal portion.

Embodiment 15: The absorbent article of any one of embodiments 9-14, wherein the waist containment member includes at least one elastic member.

Embodiment 16: The absorbent article of any one of embodiments 9-15, wherein the absorbent article further comprises: a fastening system including a pair of back fasteners disposed on opposite side edges of the absorbent article, the pair of back fasteners each including a stretch component; and wherein the waist containment member is longitudinally aligned with the stretch component of each back fastener.

Embodiment 17: The absorbent article of any one of embodiments 9-16, wherein the absorbent article includes a front waist region, a rear waist region, and a crotch region, the waist containment member being disposed in the rear waist region.

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article extending in a longitudinal direction and a lateral direction comprising:
    a chassis including a body facing surface;
    an elasticated waist containment member disposed on the body facing surface of the chassis, the waist containment member comprising:
        a first longitudinal side edge and a second longitudinal side edge, the second longitudinal side edge being opposite from the first longitudinal side edge;
        an upper lateral edge and a lower lateral edge, the upper lateral edge being opposite from the lower lateral edge, the upper lateral edge and the lower lateral edge extending in the lateral direction;
        a laterally extending proximal portion being coupled to the body facing surface of the chassis; and
        a laterally extending distal portion being free to move with respect to the chassis when the absorbent article is in the relaxed configuration to provide a pocket for exudates, the laterally extending distal portion comprising one or more laterally extending elastic members; and
    an absorbent body comprising:
        a first end edge and a second end edge;
        a pair of opposing longitudinal edges that extend between the first end edge and the second end edge;
        a first section having a first thickness;
        a second section having a second thickness, the first section and the second section each at least partially disposed under the waist containment member; and an intermediate section disposed laterally between the first section and the second section, a thickness of the intermediate section being less than the first thickness and less than the second thickness, at least a portion of the intermediate section being disposed under the waist containment member.

2. The absorbent article of claim 1, wherein the intermediate section includes a lower edge, and the lower edge of the intermediate section is not disposed under the waist containment member.

3. The absorbent article of claim 1, wherein the first thickness is substantially equal to the second thickness.

4. The absorbent article of claim 1, wherein the thickness of the intermediate section is less than 75% of the first thickness and less than 75% of the second thickness.

5. The absorbent article of claim 1, wherein the absorbent body includes at least two intermediate sections wherein a thickness of each of the at least two intermediate sections is less than the first thickness and less than the second thickness.

6. The absorbent article of claim 1, wherein a laterally extending fold separates the proximal portion from the distal portion such that the proximal portion is disposed under the distal portion.

7. The absorbent article of claim 1, wherein the absorbent article further comprises:
a fastening system including a pair of back fasteners disposed on opposite side edges of the absorbent article, the pair of back fasteners each including a stretch component; and wherein the waist containment member is longitudinally aligned with the stretch component of each back fastener.

8. The absorbent article of claim 1, wherein the absorbent article includes a front waist region, a rear waist region, and a crotch region, the waist containment member being disposed in the rear waist region.

9. The absorbent article of claim 1, wherein a lateral width of the intermediate section is greater than 25% of a lateral width of one of the first end edge and the second end edge of the absorbent body.

10. The absorbent article of claim 1, wherein a lateral width of the intermediate section is greater than 40% of a lateral width of one of the first end edge and the second end edge of the absorbent body.

11. The absorbent article of claim 1, wherein the intermediate section comprises absorbent material.

12. The absorbent article of claim 1, wherein the intermediate section comprises an embossed portion of the absorbent body.

13. The absorbent article of claim 1, wherein the waist containment member is coupled to the to the body facing surface of the chassis with adhesive such that the adhesive is disposed directly above, in a direction perpendicular to both the longitudinal direction and the lateral direction, a portion of the absorbent body having a thickness greater than the intermediate section.

* * * * *